United States Patent
Takahashi et al.

(10) Patent No.: US 9,675,715 B2
(45) Date of Patent: Jun. 13, 2017

(54) CONTRAST AGENT FOR PHOTOACOUSTIC IMAGING

(71) Applicant: CANON KABUSHIKI KAISHA, Tokyo (JP)

(72) Inventors: Atsushi Takahashi, Kyoto (JP); Satoshi Ogawa, Kyoto (JP); Fumio Yamauchi, Kyoto (JP); Kengo Kanazaki, Kyoto (JP); Daisuke Sasaguri, Yokohama (JP); Masato Minami, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/413,402

(22) PCT Filed: Jul. 17, 2013

(86) PCT No.: PCT/JP2013/004358
§ 371 (c)(1),
(2) Date: Jan. 7, 2015

(87) PCT Pub. No.: WO2014/013729
PCT Pub. Date: Jan. 23, 2014

(65) Prior Publication Data
US 2015/0290345 A1    Oct. 15, 2015

(30) Foreign Application Priority Data

Jul. 20, 2012 (JP) .................................. 2012-161643

(51) Int. Cl.
*A61K 49/22* (2006.01)

(52) U.S. Cl.
CPC .......... *A61K 49/221* (2013.01); *A61K 49/225* (2013.01)

(58) Field of Classification Search
CPC ...... A61K 49/00; A61K 49/84; A61K 49/225; A61K 49/226
See application file for complete search history.

(56) References Cited

U.S. PATENT DOCUMENTS

| | | | |
|---|---|---|---|
| 5,968,479 A | 10/1999 | Ito et al. | |
| 8,147,805 B2 | 4/2012 | Yang et al. | |
| 8,491,908 B2 * | 7/2013 | Kanazaki | C07K 17/08 424/179.1 |
| 8,652,441 B2 | 2/2014 | Fukui et al. | |
| 8,753,608 B2 | 6/2014 | Tabata et al. | |
| 2008/0308733 A1 * | 12/2008 | Doncaster | G01N 21/0303 250/343 |
| 2008/0308744 A1 | 12/2008 | Frangioni et al. | |
| 2011/0104056 A1 | 5/2011 | Hara et al. | |
| 2011/0294987 A1 | 12/2011 | Kanazaki et al. | |
| 2012/0276005 A1 | 11/2012 | Yang et al. | |
| 2013/0209367 A1 | 8/2013 | Ito et al. | |
| 2013/0224121 A1 | 8/2013 | Fukui et al. | |
| 2014/0227195 A1 | 8/2014 | Tabata et al. | |
| 2015/0157741 A1 | 6/2015 | Yamauchi et al. | |
| 2015/0165071 A1 | 6/2015 | Takahashi et al. | |

FOREIGN PATENT DOCUMENTS

| | | |
|---|---|---|
| CN | 101137398 A | 3/2008 |
| JP | 9-124599 A | 5/1997 |
| JP | 2011-184329 A | 9/2011 |
| JP | 2012-012377 A | 1/2012 |
| JP | 2012-012383 A | 1/2012 |
| WO | 2004/024191 A2 | 3/2004 |
| WO | 2005/082423 A2 | 9/2005 |
| WO | 2009/148121 A1 | 12/2009 |
| WO | 2011/057709 A1 | 5/2011 |
| WO | 2014/013730 A1 | 1/2014 |
| WO | 2014/013732 A1 | 1/2014 |

OTHER PUBLICATIONS

U.S. Appl. No. 14/413,400, filed Jan. 7, 2015, Yamauchi et al.
U.S. Appl. No. 14/413,399, filed Jan. 7, 2015, Takahashi et al.
Xueding Wang et al., "Noninvasive Photoacoustic Angiography of Animal Brains In Vivo with Near-Infrared Light and an Optical Contrast Agent," 29(7) Opt. Lett. 730-732 (Apr. 2004) (XP055079408).
Vinita M. Alexander et al., "Galactosyl Human Serum Albumin-NMP1 Conjugate: A Near Infrared (NIR)-Activatable Fluorescence Imaging Agent to Detect Peritoneal Ovarian Cancer Metastases," 23(8) Bioconjugate Chem. 1671-1679 (Jul. 2012) (XP055081842).
Lihong V. Wang et al., "Combined Photoacoustic and Molecular Fluorescence Imaging In Vivo," Proceedings of the 2005 IEEE, EMBS 27th Annual International Conference, pp. 190-192 (Sep. 2005) (XP031000945).
Chulhong Kim et al., "Handheld Array-Based Photoacoustic Probe for Guiding Needle Biopsy of Sentinel Lymph Nodes," 15(4) J. Biomed. Opt. 046010 (1-4) (Aug. 2010) (XP055065232).
First Office Action in Chinese Application No. 201380038562.9 (notified Feb. 3, 2016).
Partial English Language Translation of JP 9-124599 (May 13, 1997).

* cited by examiner

*Primary Examiner* — Michael G. Hartley
*Assistant Examiner* — Jagadishwar Samala
(74) *Attorney, Agent, or Firm* — Fitzpatrick, Cella, Harper & Scinto

(57) ABSTRACT

There is provided a contrast agent for photoacoustic imaging, the contrast agent exhibiting high tumor accumulation and high photoacoustic signal intensity even when time has passed since administration.
A contrast agent for photoacoustic imaging comprises a complex including albumin covalently bound to an organic dye that absorbs light in the near-infrared wavelength region.

10 Claims, 3 Drawing Sheets

CONTRAST AGENT FOR PHOTOACOUSTIC IMAGING

TECHNICAL FIELD

The present invention relates to a contrast agent for photoacoustic imaging.

BACKGROUND ART

A photoacoustic tomography (hereinafter, also referred to as "PAT") apparatus is known as one of apparatuses for visualizing in-vivo information. In the measurement using a PAT apparatus, an image can be obtained by measuring the intensity and the time of generation of a photoacoustic signal emitted from a substance (optical absorber) that absorbs light in an object to be measured when the object is irradiated with light, and computing a distribution of the substance in the object.

Any substance that absorbs light and emits an acoustic wave in a living body may be used as an optical absorber. For example, a blood vessel or a malignancy in the human body may be used as an optical absorber. In addition, for example, molecules of indocyanine green (hereinafter, also abbreviated as "ICG"), may be administered into the body and used as contrast agents. ICG well absorbs light in the near-infrared wavelength region, the light having little influence on the human body when the human body is irradiated with the light and having a high permeability to a living body. Thus, ICG may be used as a contrast agent in PAT apparatuses. In this specification, ICG indicates a compound represented by formula (1) described below.

[Chem. 1]

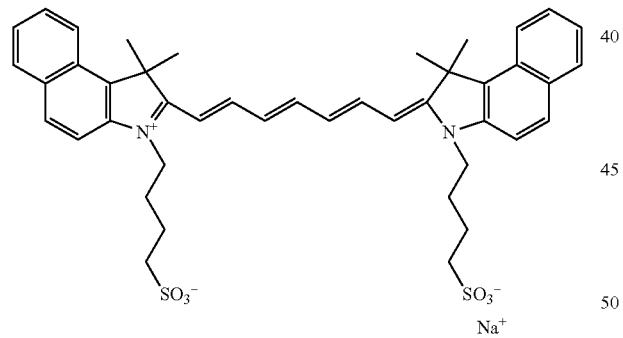

(1)

The counter ion may not be $Na^+$. Any counter ion, e.g., $H^+$ or $K^+$, may be used.

However, it is known that ICG has a short half-life of about several minutes in blood. NPL 1 reports a case of photoacoustic imaging of cerebral blood vessels of a rat with free ICG. According to this report, the photoacoustic signal intensity is reduced to a level equal to that of blood several tens of minutes after free ICG is administered in blood. This suggests that the administered substance is rapidly cleared from blood after administration.

As described above, free ICG is cleared from blood several tens of minutes after administration in blood, thus possibly resulting in a low tumor accumulation when time has passed since administration.

CITATION LIST

Non Patent Literature

NPL 1: Optics Letters, Vol. 29, Issue 7, pp. 730-732 (2004)

SUMMARY OF INVENTION

Technical Problem

Accordingly, aspects of the present invention provide a contrast agent for photoacoustic imaging, the contrast agent exhibiting high tumor accumulation and high photoacoustic signal intensity even when time has passed since administration.

Solution to Problem

A contrast agent for photoacoustic imaging according to an aspect of the present invention comprises a complex including albumin bound to a near-infrared absorbing organic dye.

A contrast agent for photoacoustic imaging according to another aspect of the present invention comprises a complex represented by formula (I):

[Chem. 2]

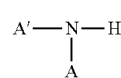

(I)

In formula (I), A represents a site of albumin with one amino group removed. A' represents formula (i) or (ii). "*" in each of formulae (i) and (ii) is bound to a nitrogen atom (N) in formula (I).

[Chem. 3]

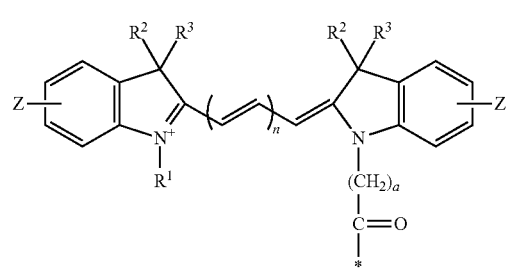

(i)

[Chem. 4]

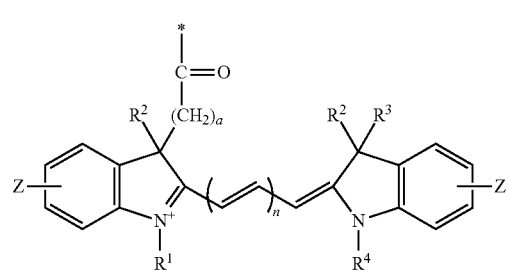

(ii)

In formulae (i) and (ii), Z's each represent a hydrogen atom, a sulfonic group, or a cyclic aromatic ring selected from the group consisting of a benz[e]indole ring, a benz[f]indole ring, and a benz[g]indole ring formed together with an indole ring bound to a corresponding one of Z's. The hydrogen atoms of the cyclic aromatic ring each may be replaced with an alkyl group having 1 to 10 carbon atoms, an alkoxy group having 1 to 10 carbon atoms, or a sulfonic group.

In formulae (i) and (ii), $R^1$'s each represent an alkyl group having 1 to 10 carbon atoms or $—(CH_2)_b—SO_3^-$ (wherein b represents an integer of 1 to 10).

When $R^1$'s each represent an alkyl group, a halide ion or an organic acid ion may be contained as a counter ion. $R^2$'s and $R^3$'s each independently represent a hydrogen atom, an alkyl group having 1 to 10 carbon atoms, an alkoxy group having 1 to 10 carbon atoms, $—(CH_2)_b—SO_3^-$ (wherein b represents an integer of 1 to 10), or $—(CH_2)_b—SO_3X$ (wherein b represents an integer of 1 to 10, and X represents sodium, potassium, ammonium, triethylammonium, lysine, or arginine).

In formulae (i) and (ii), a's each represent an integer of 1 to 10, and n's each represent 2 or 3.

In formula (ii), $R^4$ represents an alkyl group having 1 to 10 carbon atoms or $—(CH_2)_b—SO_3X$ (wherein b represents an integer of 1 to 10, and X represents sodium, potassium, ammonium, triethylammonium, lysine, or arginine).

Advantageous Effects of Invention

A contrast agent for photoacoustic imaging according to aspects of the present invention contains a complex including albumin bound to an organic dye, such as ICG, the dye absorbing light in the near-infrared wavelength region; hence, the contrast agent exhibits high accumulation in a tumor and high intensity of a photoacoustic signal emitted from the tumor, compared with the case where free ICG is administered.

DESCRIPTION OF EMBODIMENTS

Figure 1A:
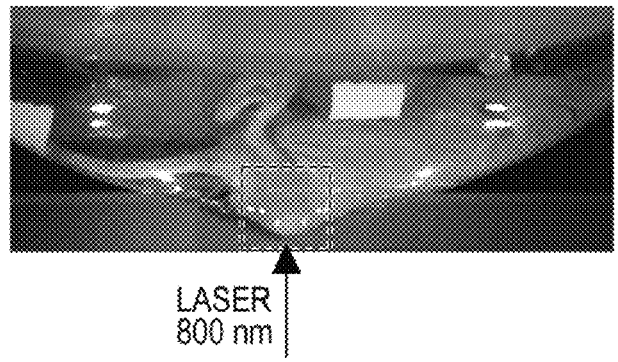
FIG. 1A illustrates the results of measurements of time-dependent photoacoustic imaging of a tumor site of a tumor-bearing model mouse to which ICG-HSA (7) prepared in an example of the present invention is administered.
Figure 1B:
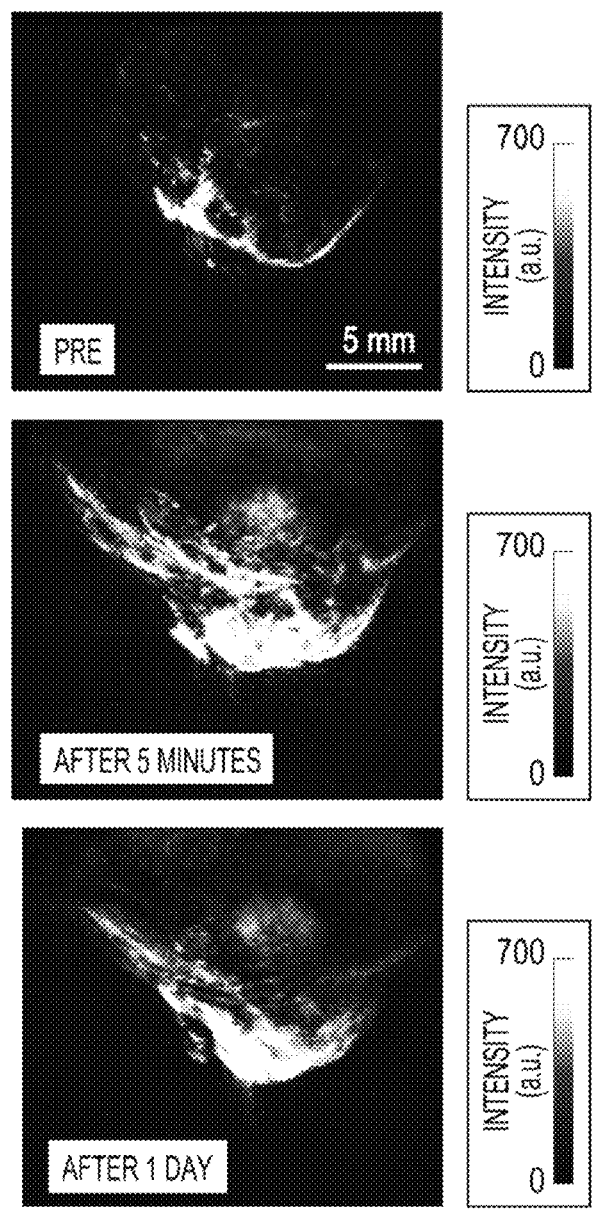
FIG. 1B illustrates the results of measurements of time-dependent photoacoustic imaging of a tumor site of a tumor-bearing model mouse to which ICG-HSA (7) prepared in an example of the present invention is administered.

A contrast agent for photoacoustic imaging (hereinafter, also abbreviated as "PAI") according to an embodiment of the present invention will be described below.

The contrast agent for PAI according to this embodiment includes a complex including albumin covalently bound to an organic dye that absorbs light in the near-infrared wavelength region (hereinafter, also abbreviated as a "near-infrared absorbing organic dye"). In this specification, light in the near-infrared wavelength region refers to light having a wavelength of 600 nm to 1300 nm.

In the case where a near-infrared absorbing organic dye, such as ICG, is administered in blood, the dye is easily adsorbed on protein in blood and excreted from the body. Furthermore, the near-infrared absorbing organic dye may react with water molecules in blood to decompose. Thus, even if a free near-infrared absorbing organic dye is administered in blood of a living body, the dye exhibits short retention in blood and low accumulation in a tumor. Accordingly, in the case where a free near-infrared absorbing organic dye is used as a contrast agent for photoacoustic imaging, the intensity of the photoacoustic signal emitted from a tumor is low.

In the contrast agent for PAI according to this embodiment, albumin inhibits the adsorption of protein in blood on the near-infrared absorbing organic dye because the near-infrared absorbing organic dye is covalently bound to albumin. Thus, in the case where the contrast agent for PAI according to this embodiment is administered in blood of a living body, the contrast agent does not easily adsorb on protein in blood and is not easily excreted from the body. Furthermore, water molecules in blood do not easily approach the near-infrared absorbing organic dye because the near-infrared absorbing organic dye and albumin are covalently bound together; hence, the near-infrared absorbing organic dye is not easily decomposed. In addition, albumin has a half-life of about 20 days or less and is thus stable in a living body. Thus, the retention in blood should be improved, compared with the case where a free near-infrared absorbing organic dye is administered. For these reasons, the contrast agent for PAI according to this embodiment exhibits longer retention in blood and high accumulation in a tumor, compared with the case of administration of a free near-infrared absorbing organic dye. Thus, the effect of increasing the intensity of a photoacoustic signal emitted from the tumor should be provided.

With respect to the complex of the contrast agent for PAI according to this embodiment, at least one albumin and at least one near-infrared absorbing organic dye may be covalently bound together. A plurality of albumins and a plurality of near-infrared absorbing organic dyes may be covalently bound together. In the case where the complex includes albumin and a plurality of near-infrared absorbing organic dyes, at least one near-infrared absorbing organic dye may be covalently bound to albumin, and the remaining near-infrared absorbing organic dyes may be noncovalently bound. Similarly, in the case where the complex includes a near-infrared absorbing organic dye and a plurality of albumins, at least one albumin may be covalently bound to the near-infrared absorbing organic dye, and the remaining albumins may be noncovalently bound.

Strictly speaking, "albumin and the near-infrared absorbing organic dye are covalently bound together" used in an embodiment of the present invention and in this specification indicates that a site (this may also be referred to as a "group") of albumin with a portion (typically, H or OH) of albumin removed and a site of the near-infrared absorbing organic dye with a portion (typically, H or OH) of the near-infrared absorbing organic dye removed are covalently bound. The "complex" can also be referred to as a "molecule" from another point of view.

Dye Labeling Index

In this specification, the number of the near-infrared absorbing organic dyes covalently bound to one albumin is referred to as a "dye labeling index". In the contrast agent for PAI according to this embodiment, the dye labeling index may be higher than 0.9 and lower than 3.1. Furthermore, in this embodiment, the dye labeling index is preferably 1.6 or more and 3.0 or less. The reason for this is that when the dye labeling index falls within the range described above, high tumor accumulation is obtained. The dye labeling index was calculated by measuring concentrations of the near-infrared absorbing organic dye and albumin in a sample and determining the ratio of the concentration of the near-infrared absorbing organic dye to the concentration of albumin (the concentration of the near-infrared absorbing organic dye/the concentration of albumin) The concentration of the near-infrared absorbing organic dye was calculated from the absorbance at a specific absorption wavelength of the dye. For example, when ICG-Sulfo-OSu (a compound represented by formula (2) described below) is used, a wavelength of 800 nm may be used as the specific absorption wavelength. When a compound represented by formula (5) is used, a wavelength of 750 nm may be used as the specific absorption wavelength. However, another specific absorption wavelength may be used. The concentration of albumin may be determined by, for example, the BCA assay.

The contrast agent for PAI according to this embodiment may contain a complex represented by formula (I),

[Chem. 5]

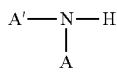

(I)

In formula (I), A represents a site of albumin with one amino group removed. A' represents formula (i) or (ii). "*" in each of formulae (i) and (ii) is bound to a nitrogen atom (N) in formula (I).

In this specification, "*" is equivalent to the following symbol:

[Chem. 6]

The symbol is illustrated in the structural formulae:

[Chem. 7]

(i)

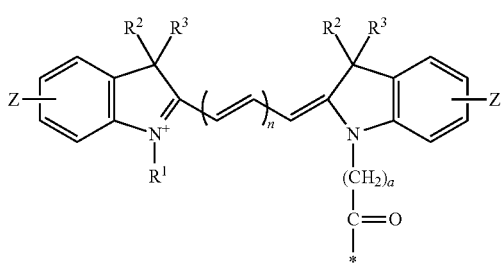

[Chem. 8]

(ii)

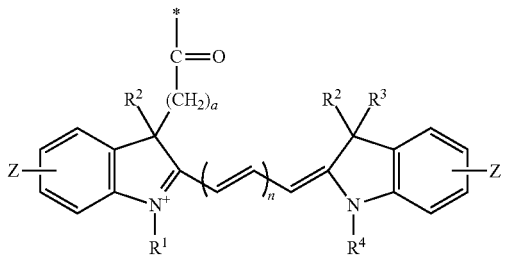

In formulae (i) and (ii), Z's each represent a hydrogen atom, a sulfonic group, or a cyclic aromatic ring selected from the group consisting of a benz[e]indole ring, a benz[f]indole ring, and a benz[g]indole ring formed together with an indole ring bound to a corresponding one of Z's. The hydrogen atoms of the cyclic aromatic ring each may be replaced with an alkyl group having 1 to 10 carbon atoms, an alkoxy group having 1 to 10 carbon atoms, or a sulfonic group.

In formulae (i) and (ii), $R^1$'s each represent an alkyl group having 1 to 10 carbon atoms or —$(CH_2)_b$—$SO_3^-$ (wherein b represents an integer of 1 to 10). When $R^1$'s each represent an alkyl group, a halide ion, e.g., a chloride ion, a bromide ion, or an iodide ion, or an organic acid ion, e.g., an acetate ion, a tartrate ion, or a succinate ion, may be contained as a counter ion. $R^2$'s and $R^3$'s each independently represent a hydrogen atom, an alkyl group having 1 to 10 carbon atoms, an alkoxy group having 1 to 10 carbon atoms, —$(CH_2)_b$—$SO_3^-$ (wherein b represents an integer of 1 to 10), or —$(CH_2)_b$—$SO_3X$ (wherein b represents an integer of 1 to 10, and X represents sodium, potassium, ammonium, triethylammonium, lysine, or arginine).

In formulae (i) and (ii), a's each represent an integer of 1 to 10, and n's each represent 2 or 3.

In formula (ii), $R^4$ represents an alkyl group having 1 to 10 carbon atoms or —$(CH_2)_b$—$SO_3X$ (wherein b represents an integer of 1 to 10, and X represents sodium, potassium, ammonium, triethylammonium, lysine, or arginine). In formula (I), a portion indicated by A-N—H corresponds to the site of albumin with a portion of albumin removed. A' corresponds to the site of the near-infrared absorbing organic dye with a portion of the near-infrared absorbing organic dye removed.

In the contrast agent for PAI according to this embodiment, formula (i) may be represented by any one of formulae (i-1) to (i-6) described below.

[Chem. 9]

(i-1)

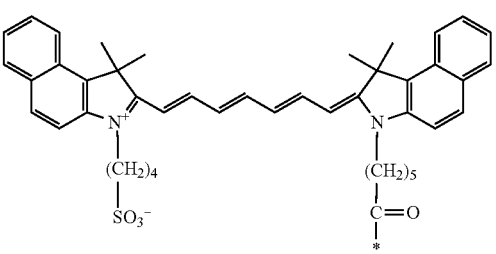

[Chem. 10]
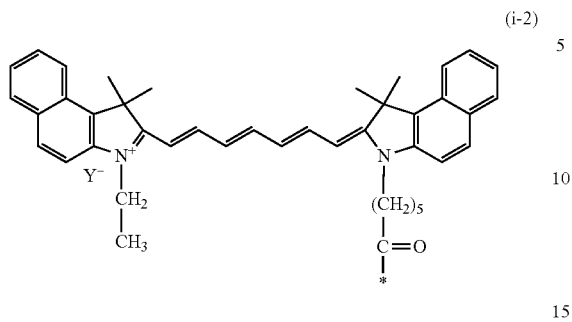
(i-2)
In formula (i-2), Y⁻ represents a halide ion, e.g., a chloride ion, a bromide ion, or an iodide ion, or an organic acid ion, e.g., an acetate ion, a tartrate ion, or a succinate ion.
[Chem. 11]
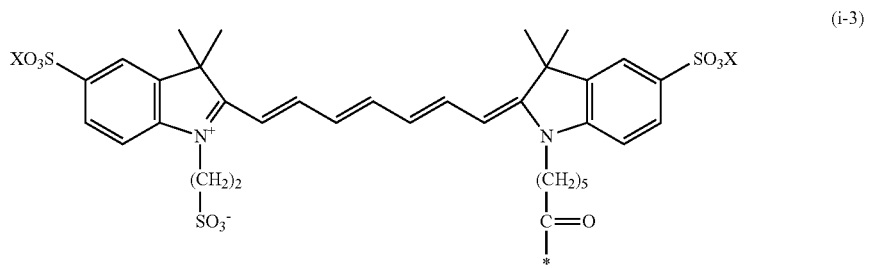
(i-3)
[Chem. 12]
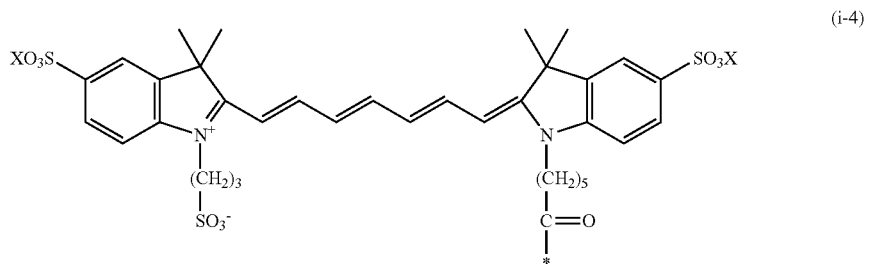
(i-4)
[Chem. 13]
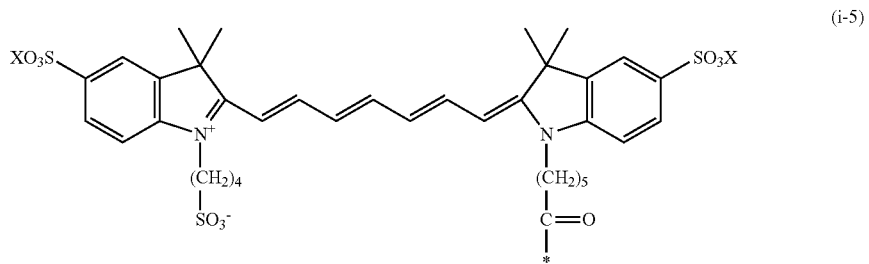
(i-5)

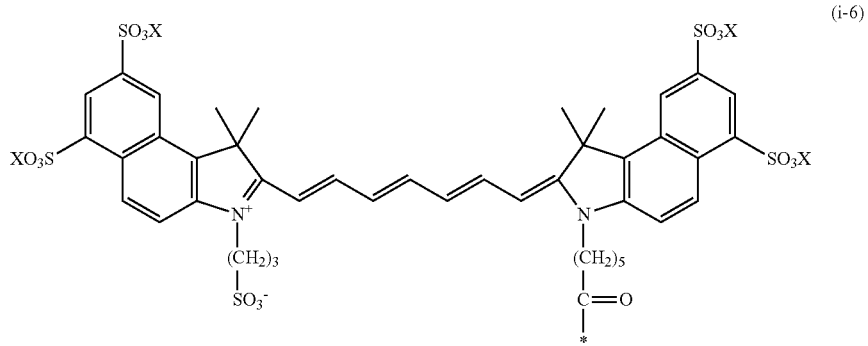

(i-6)

In formulae (i-3) to (i-6), X's each represent sodium, potassium, ammonium, triethylammonium, lysine, or arginine.

In the contrast agent for PAI according to this embodiment, formula (ii) may be represented by formula (ii-1) or (ii-2) described below.

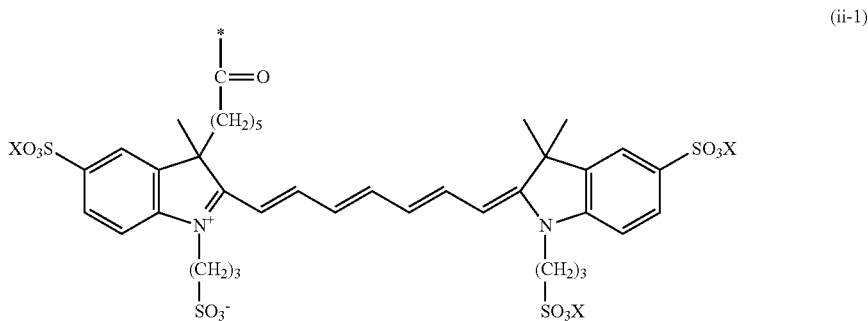

(ii-1)

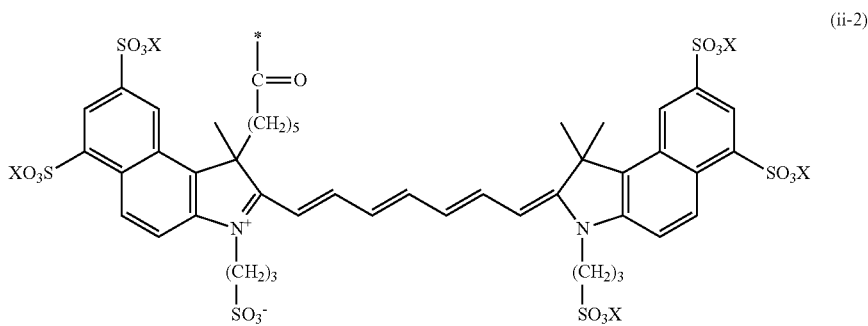

(ii-2)

In formulae (ii-1) and (ii-2), X's each represent sodium, potassium, ammonium, triethylammonium, lysine, or arginine.

In formulae (i) and (ii), a's may each represent an integer of 2 to 6. In formulae (i) and (ii), b's in $R^1$'s, $R^2$'s, and $R^3$'s may each represent an integer of 2 to 6.

In formulae (i) and (ii), when a's and b's each represent 6 or less, the hydrophobicity of the complex is not high. Thus, the nonspecific adsorption of the complex is less likely to occur in a living body.

In this embodiment, the complex may be represented by formula (I-1) described below.

[Chem. 17]

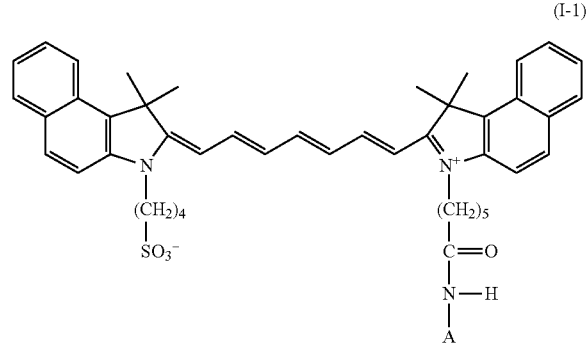

(I-1)

In formula (I-1), A represents a site of albumin with one amino group of albumin removed.

The contrast agent for PAI according to this embodiment may contain a capture molecule that binds specifically to a target site.

Albumin

Albumin according to this embodiment is an abundant protein in blood (35 to 50 g/L), the protein having a molecular mass of 66.5 kDa and containing 585 amino acids in its complete sequence. Albumin is localized in vivo to play many roles, such as osmotic control. As albumin according to this embodiment, human serum albumin (HSA) and bovine serum albumin (BSA) may be used. A variant of HSA or BSA may also be used. A fragment thereof may also be used. As albumin according to this embodiment, HSA, a variant of HSA, a fragment of HSA, or a fragment of a variant of HSA, which is believed to be safe for the human body, may be used. Albumin according to this embodiment may be an extract from human blood or a product from *Escherichia coli* or the like. Albumin according to this embodiment has a homology of at least 95% or more, as compared with the complete sequence or a partial sequence from the complete sequence of HSA. Albumin has a plurality of lysine residues or a free cysteine residue at positions where the near-infrared absorbing organic dye is accessible. In the case where a chemical bond between albumin and the near-infrared absorbing organic dye is formed, for example, an amide bond between an amino group of a lysine residue of albumin and a carboxy group of the near-infrared absorbing organic dye is exemplified.

Near-Infrared Absorbing Organic Dye

In this embodiment, the near-infrared absorbing organic dye is not particularly limited as long as it is an organic dye that absorbs light in the near-infrared wavelength region to emit an acoustic wave.

Examples of the near-infrared absorbing organic dye in this embodiment include azine-based dyes, acridine-based dyes, triphenylmethane-based dyes, xanthene-based dyes, porphyrin-based dyes, cyanine-based dyes, phthalocyanine-based dyes, styryl-based dyes, pyrylium-based dyes, azo-based dyes, quinone-based dyes, tetracycline-based dyes, flavone-based dyes, polyene-based dyes, BODIPY (registered trademark)-based dyes, and indigoid-based dyes.

Examples of the cyanine-based dyes include indocyanine green (ICG), Alexa Fluor (registered trademark)-based dyes, such as Alexa 750, (manufactured by Invitrogen Corporation); Cy (registered trademark)-based dyes (manufactured by GE Healthcare Biosciences K.K.); IR-783, IR-806, and IR-820 (manufactured by Sigma-Aldrich Japan K.K.); IRDye 800CW and IRDye 800RS (registered trademark) (manufactured by LI-COR, Inc.); ADS780WS, ADS795WS, ADS830WS, and ADS832WS (manufactured by American Dye Source Inc.); Hylight (manufactured by Dojindo Laboratories); and DyLight (manufactured by Thermo Fisher Scientific Inc).

In this embodiment, the near-infrared absorbing organic dye may be represented by formula (II) described below.

[Chem. 18]

B-B'     (II)

In formula (II), B represents formula (i) or (ii) described above. B' represents any one of formulae (iii) to (vi) described below.

*'s in formulae (i) and (ii) each bind to B' of formula (II).
*'s in formulae (iii) to (vi) each bind to B of formula (II).

[Chem. 19]

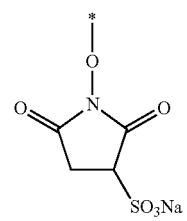

(iii)

[Chem. 20]

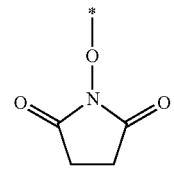

(iv)

[Chem. 21]

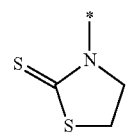

(v)

[Chem. 22]

*—OH     (vi)

As an example of formula (II), a compound represented by formula (2) (ICG-Sulfo-OSu (registered trademark, manufactured by Dojindo Laboratories)), a compound represented by formula (3), a compound represented by formula (4), a compound represented by formula (5), a compound represented by formula (6), or a compound represented by formula (7) may be used.

[Chem. 23]
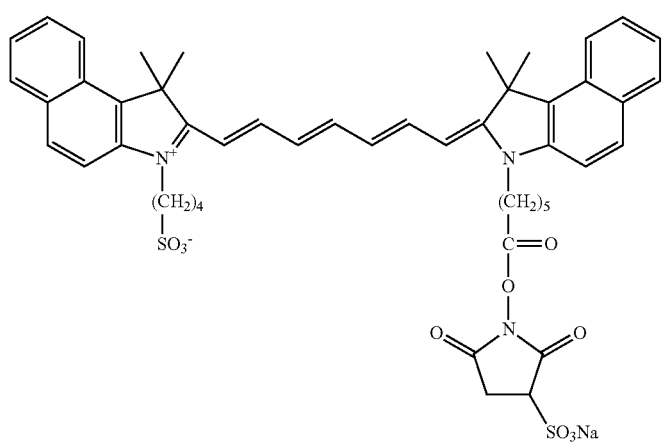
(2)
[Chem. 24]
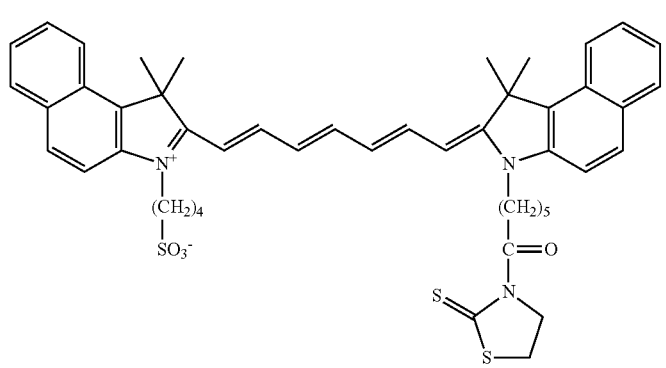
(3)
[Chem. 25]
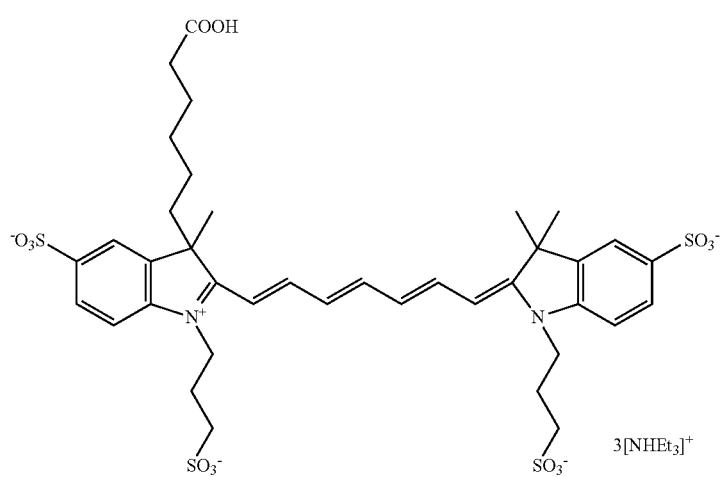
(4)

-continued
[Chem. 26]
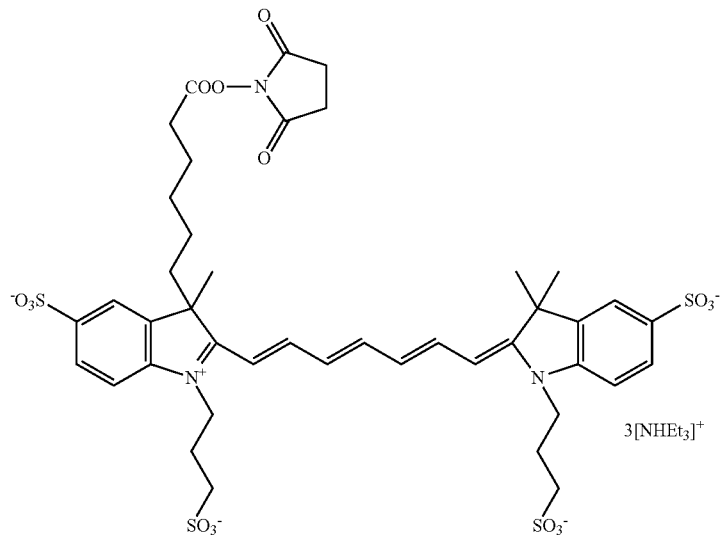
(5)
[Chem. 27]
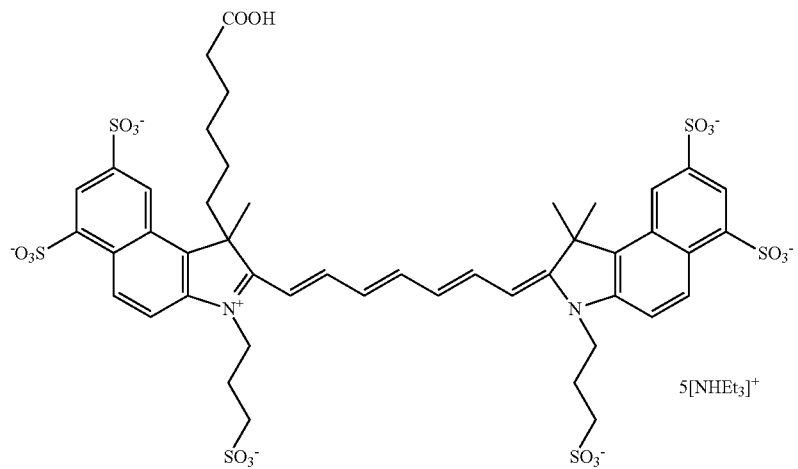
(6)

[Chem. 28]

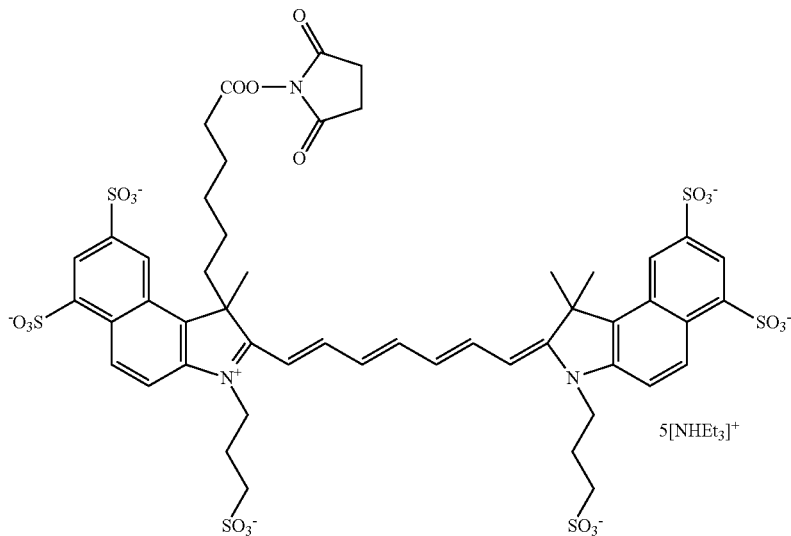

(7)

Method for Preparing Complex

In this embodiment, albumin and the near-infrared absorbing organic dye may be covalently bound together by a known coupling reaction with an amino group, a thiol group, a carboxy group, or a hydroxy group provided therebetween. A plurality of amino groups are present in albumin and react efficiently and selectively in a weak alkaline pH region. The near-infrared absorbing organic dye bound to albumin by the reaction may be washed and purified by a known protein purification method, for example, ultrafiltration or size-exclusion column chromatography. With respect to the bond between albumin and the near-infrared absorbing organic dye, the amino group, the thiol group, the carboxy group, or the hydroxy group present on the surface of albumin may be directly bound to a derivative of the near-infrared absorbing organic dye. Alternatively, albumin and the near-infrared absorbing organic dye may be bound together with any of a variety of cross-linkers.

Hydrodynamic Average Particle Size

In the contrast agent for PAI according to this embodiment, the complex may be in the form of particles. Each of the particles may be any of shapes, such as spherical, elliptic, planar, and one-dimensional string-like shapes. In the case where the complex is in the form of particles, the hydrodynamic average particle size (hereinafter, abbreviated simply as "particle size", in some cases) may be less than 1000 nm when measured by a dynamic light scattering method. A particle size of less than 1000 nm results in the accumulation of a large number of particles in a tumor site by the enhanced permeability and retention (EPR) effect, compared with normal sites in a living body. The contrast agent for PAI accumulated in the tumor site results in the specific visualization of the tumor site by the use of a photoacoustic imaging apparatus. The particle size of the particles is preferably 200 nm or less and more preferably 50 nm or less when measured by the dynamic light scattering method. The reason for this is presumably that when the particle size of the particles is 200 nm or less, the contrast agent for PAI according to this embodiment is less likely to be taken up by macrophages in blood, thereby increasing the retention in blood. In addition, when the particle size of the particles is 50 nm or less, the tissue permeability of the particles should be increased, thereby increasing the accumulation of the particles that have reached a target site.

In this embodiment, the particle size of the particles may be determined by measuring the hydrodynamic average particle size using the dynamic light scattering (DLS) method with a dynamic light scattering spectrophotometer (DLS-8000, manufactured by Otsuka Electronics Co., Ltd).

The contrast agent for PAI according to this embodiment may contain a dispersion medium in addition to the complex. The PAI is a concept including photoacoustic tomography. Examples of the dispersion medium include physiological saline, distilled water for injection, phosphate-buffered saline, and an aqueous glucose solution. The contrast agent for PAI according to this embodiment may contain a pharmaceutically acceptable additive, such as a vasodilator, as needed.

In the contrast agent for PAI according to this embodiment, the particles may be dispersed in the dispersion medium in advance. Alternatively, the particles and the dispersion medium may be prepared as a kit, and the particles may be dispersed in the dispersion medium prior to the administration of the contrast agent into a living body.

In the contrast agent for PAI according to this embodiment, a larger number of the particles can be accumulated in a tumor site than in normal sites in a living body by the EPR effect when the contrast agent is administered into a living body. Thus, after the particles are administered into the body, in the case where the body is irradiated with light and where an acoustic wave emitted from the body is detected, the intensity of an acoustic wave emitted from the tumor site can be increased, compared with the intensity of acoustic waves emitted from the normal sites. Hence, the contrast agent for PAI according to this embodiment may be used for tumor imaging.

The contrast agent for PAI according to this embodiment may also be used to image a lymph node. In particular, the contrast agent may be used as a contrast agent for a sentinel lymph node (hereinafter, abbreviated as "SLN", in some cases). When a near-infrared absorbing organic dye, such as ICG, is used as a contrast agent for the sentinel lymph node, the near-infrared absorbing organic dye administered into the body is rapidly transferred into blood and cleared from the body. This disadvantageously limits the period of observation. The contrast agent for PAI according to this embodiment has a larger molecular size than the near-infrared absorbing organic dye, thus reducing the rate of diffusion in tissues. As a result, the retention time in the sentinel lymph node should be extended. Thus, the contrast agent for PAI according to this embodiment may be used to image a lymph node, in particular, a sentinel lymph node.

Capture Molecule

The capture molecule in this embodiment is, for example, a substance that binds specifically to a target site, such as a tumor, or a substance that binds specifically to a substance present around a target site. The capture molecule may be freely selected from biomolecules and chemical substances, such as pharmaceuticals. Specific examples thereof include proteins, antibodies, antibody fragments, enzymes, biologically active peptides, glycopeptides, sugar chains, lipids, and molecule-recognizing compounds. These substances may be used separately or in combination. The use of the particles to which the capture molecules are chemically bonded enables the specific detection of a target site and the tracing of the dynamics, localization, efficacy of medicine, metabolism, and so forth of the target substance. In this embodiment, protein refers to a compound in which 90 or more natural or non-natural amino acids are connected by amide bonds. In this embodiment, polypeptide refers to a compound in which 30 or more and less than 90 natural or non-natural amino acids are connected by amide bonds. In this embodiment, peptide refers to a compound in which less than 30 natural or non-natural amino acids are connected by amide bonds. In this embodiment, protein, polypeptide, and peptide are classified by the number of amino acids connected, regardless of the presence or absence of various modifications. In this embodiment, the capture molecule may be protein, polypeptide, or peptide. In this embodiment, the capture molecule may be an antibody, which is a protein. In particular, the capture molecule may be a single-chain antibody.

Another embodiment according to the present invention is a contrast agent for photoacoustic imaging, in which the contrast agent comprises a complex which is represented by formula (III):

[Chem. 29]

ALB-L-C  (III)

In formula (III), ALB represents the albumin which is covalently bound by the organic dye; C represents a capture molecule; and L represents a linker, ALB being bound to L, and L being bound to C.

In this embodiment, the capture molecule may be a protein, a polypeptide, or a peptide. The protein may be a single-chain antibody.

In this embodiment, L in formula (III) may include one or more succinimidyl groups at an end and one or more maleimido groups at the other end.

In this embodiment, L in formula (III) may include one or more succinimidyl groups at the end, one or more maleimido groups at the other end, and one or more ethylene glycol moieties.

In this embodiment, L in formula (III) may represent succinimidyl-[(N-maleimidopropionamido)-diethyleneglycol]ester or SUNBRIGHT MA-100TS.

In this embodiment, L in formula (III) may represent succinimidyl 4-[N-maleimidomethyl]cyclohexane-1-carboxylate.

In this embodiment, L in formula (III) may include two or more succinimidyl groups at an end.

In this embodiment, L in formula (III) may include two or more succinimidyl groups at an end and one or more ethylene glycol moieties.

In this embodiment, L in formula (III) may represent bis-N-succinimidyl-(pentaethylene glycol) ester.

Addition Agent

The contrast agent for photoacoustic imaging according to the present embodiment may contain an addition agent used in freeze-drying. Examples of addition agents include glucose, lactose, mannitol, polyethylene glycol, glycine, sodium chloride, and sodium hydrogen phosphate. One type of addition agent may be used alone or some types may be used in combination.

Photoacoustic Imaging Method

A method for detecting the contrast agent for PAI according to this embodiment, the contrast agent being administered into a living body, with a photoacoustic imaging apparatus will be described below. The method for detecting the contrast agent for PAI according to this embodiment includes steps (a) and (b) described below. However, the photoacoustic imaging method according to this embodiment may include a step other than the following steps:

(a) a step of irradiating a subject into which the contrast agent for PAI according to this embodiment has been administered with light in a wavelength region of 600 nm to 1300 nm; and (b) a step of detecting an acoustic wave emitted from the contrast agent present in the subject.

The photoacoustic imaging method according to this embodiment may include a step of reconstituting a spatial photoacoustic signal intensity distribution on the basis of the wavelength, the phase, the time information, and so forth of the resulting acoustic wave obtained in step (b). Three-dimensional image reconstruction may be performed on the basis of the wavelength, the phase, and the time information of the acoustic wave obtained in step (b). Data obtained by the image reconstruction may be in any form as long as the positional information on the photoacoustic signal intensity distribution can be determined. For example, the photoacoustic signal intensity may be expressed in three-dimensional space or on a two-dimensional surface. Furthermore, the information of the same observation object is acquired by another imaging method, and the positional relationship between the information and the photoacoustic signal intensity distribution can be acquired.

In step (a) described above, a subject to which the contrast agent for PAI according to this embodiment is administered by a method, for example, oral administration or injection may be used.

In step (b) described above, an apparatus configured to generate light with which the subject is irradiated, and an apparatus configured to detect an acoustic wave emitted from the contrast agent for PAI according to this embodiment are not particularly limited.

As a light source configured to emit light with which the subject is irradiated in step (b), any light source may be used without limitation as long as the subject can be irradiated with pulsed laser light having at least one wavelength selected from the range of 600 nm to 1300 nm. As the apparatus configured to emit pulsed laser light, for example, a titanium-sapphire laser (LT-2211-PC, manufactured by Lotis Ltd.), OPO laser (LT-2214 OPO, manufactured by Lotis Ltd.), or an alexandrite laser may be used.

The apparatus configured to detect an acoustic wave is not particularly limited, and any of a variety of apparatuses may be used. For example, a commercially available photoacoustic imaging apparatus (Nexus128, manufactured by Endra Inc.) may be used.

By employing the imaging method using the contrast agent for PAI according to this embodiment, a target site, for example, a tumor, a lymph node, or a blood vessel, can be imaged through steps (a) and (b).

EXAMPLES

While the present invention is described in more detail below by examples, the present invention is not limited to these examples. Materials, composition conditions, reaction conditions, and so forth may be freely changed to the extent that dye-modified albumin having an equivalent function and effect is prepared.

Method for Measuring Photoacoustic Signal Intensity

In examples of the present invention, the photoacoustic signal intensity was measured as described below.

A commercially available photoacoustic imaging apparatus (Nexus128, manufactured by Endra Inc.) was used. Photoacoustic signals were measured at predetermined timings before and after the administration of a prepared contrast agent for PAI, and three-dimensional reconstruction data was acquired for each timing. The photoacoustic signal intensity in a region of interest (ROI) was measured on the basis of the resulting three-dimensional reconstruction data using software (GEHC MICROVIEW, GE Healthcare) or the like.

Calculation of Dye Labeling Index

In examples of the present invention, the dye labeling index to albumin was calculated by measuring the absorbance of a sample. A dye concentration in the sample was calculated from absorbance at a specific absorption wavelength of the dye used. Specifically, when ICG-Sulfo-OSu (compound represented by formula (2) described above) was used, the absorbance was measured at 800 nm. When the compound represented by formula (5) described above was used, the absorbance was measured at 750 nm. The concentration of ICG was determined by diluting the sample with 5% SDS, measuring the absorbance, and calculating the concentration of ICG from a previously formed calibration curve of the dye in SDS. The concentration of HSA was calculated by the BCA assay.

Evaluation Example of Amount Transferred into Tumor Mass

In examples of the present invention, the evaluation of the contrast agent for PAI into a tumor mass was performed using tumor-bearing mice. The tumor-bearing mice were prepared by subcutaneously implanting a human gastric cancer cell line (N87) or a human cervical cancer cell line (HeLa) into nude mice. Then 130 nmol of a contrast agent in terms of the amount of the dye was administered into each of the tumor-bearing mice. Photoacoustic imaging was performed 5 minutes after the administration and 1 day after the administration. As a comparative example, fluorescence imaging of the tumor-bearing mice was performed 1 day after the administration. Fluorescence imaging was performed with IVIS (registered trademark) Imaging System to measure fluorescence intensity in a region of interest (ROI) of the tumor site.

Evaluation Example of Accumulation in Sentinel Lymph Node

In examples of the present invention, the transfer of the contrast agent for PAI into a sentinel lymph node (SLN) was evaluated by the use of a mouse popliteal lymph node. Ten microliters of the contrast agent was administered subcutaneously into the plantar surface of a nude mouse. Photoacoustic imaging of the mouse popliteal lymph node was performed after 1 day.

As a comparative example, mouse popliteal lymph nodes were removed 1 day after the administration of various contrast agents, homogenized, and extracted. The resulting extracts were subjected to absorbance measurement.

Accumulation rates were each calculated on the basis of the following formula:

Accumulation rate={(absorbance of removed mouse popliteal lymph node)/(absorbance corresponding to amount of sample administered)}×100

After the calculation of the accumulation, the accumulation ratios of various materials were calculated when the accumulation 1 day after the administration of ICG was defined as 1.

Example

A compound according to this embodiment is a compound in which an amino group on the surface of HSA is covalently bound to a near-infrared absorbing organic dye. A typical structure of ICG-HSA is represented by formula (IV). A typical structure of ICG'-HSA is represented by formula (V).

[Chem. 30]

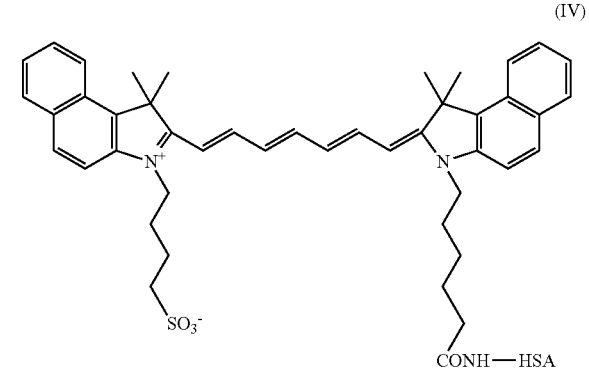

(IV)

[Chem. 31]

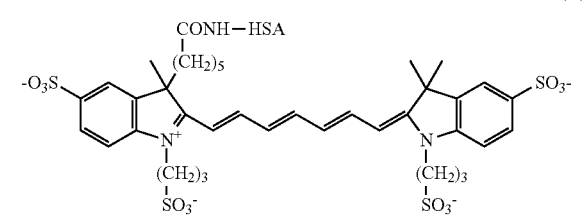

(V)

Preparation of Albumin Bound to Near-Infrared Absorbing Organic Dye

Human serum albumin (albumin from human serum: HSA, available from SIGMA, hereinafter, abbreviated simply as "HSA") was dissolved in bicarbonate buffer solutions (pH: 9.4) in a concentration of 10 mg/mL to prepare HSA solutions. Then 1 mg of the compound represented by formula (2) (ICG-Sulfo-OSu, registered trademark, manufactured by Dojindo Laboratories) was dissolved in 0.1 mL of dimethyl sulfoxide (DMSO), and 1 mg of the compound represented by formula (5) was dissolved in 0.1 mL of DMSO. These solutions were added to the respective HSA solutions. The resulting mixtures were allowed to stand at 37 degrees Celsius for 3 hours. The resulting reaction mixtures were subjected to gel filtration (PD-10) and ultrafiltration (50 kDa), so that the replacement with HEPES buffer solutions (pH: 7.6) and the separation of unreacted substances were performed. Ultimately, compounds in which near-infrared absorbing organic dyes and HSA were covalently bound were prepared. Tables 1 and 2 describe dye labeling indices of the compounds prepared at different molar concentrations of the raw materials fed for reaction. The specific chemical structure of the compound according to this embodiment is represented by formula (IV). In Table 2, the compound in which the compound represented by formula (5) is bound to HSA is expressed as ICG'-HSA. The specific chemical structure of ICG'-HSA is represented by formula (V).

As is clear from Tables 1 and 2, the dye labeling index can be changed in any range by changing the feed molar ratio of the dye derivative to HSA. With respect to samples in which the molar ratios of the dye to HSA were 80:1 and 100:1, the filtrates obtained by sterile filtration did not exhibit absorbance at the specific absorption wavelength of the dye; hence, the dye labeling index was not calculated.

TABLE 1

| Sample name | Feed molar ratio (ICG-Sulfo-Osu:HSA) | Dye labeling index |
|---|---|---|
| ICG-HSA (1) | 1:1 | 0.9 |
| ICG-HSA (2) | 2:1 | 1.4 |
| ICG-HSA (3) | 3:1 | 1.6 |
| ICG-HSA (7) | 7:1 | 2.3 |
| ICG-HSA (17.5) | 17.5:1 | 3.0 |
| ICG-HSA (50) | 50:1 | 3.1 |
| ICG-HSA (80) | 80:1 | N.D. |
| ICG-HSA (100) | 100:1 | N.D. |

(N.D.) = not detected

TABLE 2

| Sample name | Feed molar ratio (compound of formula 5:HSA) | Dye labeling index |
|---|---|---|
| ICG'-HSA (1) | 1:1 | 0.6 |
| ICG'-HSA (3) | 3:1 | 1.2 |
| ICG'-HSA (9) | 9:1 | 2.0 |
| ICG'-HSA (24) | 24:1 | 2.7 |

Measurement of Particle Size

The hydrodynamic average particle size of ICG-HSA (7) prepared by the foregoing method was measured with a dynamic light scattering spectrophotometer (DLS-8000, manufactured by Otsuka Electronics Co., Ltd). Table 3 describes the results. As comparative examples, the average particle sizes of ICG (available from Pharmaceutical and Medical Device Regulatory Science of Japan), HSA, ICG-HSA (7)-encapsulating liposome particles, and ICG-encapsulating micellar particles are also described. The ICG-HSA (7)-encapsulating liposome particles refer to particles in which ICG-HSA (7) prepared by the foregoing method is encapsulated in phospholipid liposome by a known method. The ICG-encapsulating micellar particles refer to micellar particles in which ICG is contained in surfactant micelles by a known emulsification technique.

TABLE 3

| | Material | Hydrodynamic average particle size |
|---|---|---|
| Comparative Example 1 | ICG | unmeasurable |
| Comparative Example 2 | HSA | 7.7 nm |
| Comparative Example 3 | ICG-HSA (7)-encapsulating liposome particles | 93 nm |
| Comparative Example 4 | ICG-encapsulating micellar particles | 109 nm |
| Example | ICG-HSA (7) | 20 nm |

Photoacoustic Imaging of Tumor

First, 130 nmol of ICG-HSA (7) in terms of the amount of the dye was administered to a tumor-bearing mouse into which a HeLa cell line was implanted. Photoacoustic imaging was performed with a commercially available photoacoustic imaging apparatus (Nexus128, manufactured by Endra Inc.) before the administration, 5 minutes after the administration, and 1 day after the administration. The measurement wavelength was 800 nm. Table 4 describes the relative photoacoustic signal intensity at the tumor site when the photoacoustic signal intensity measured before the administration of ICG-HSA (7) was defined as 1. Table 4 demonstrates that the photoacoustic signal intensity at the tumor site increased markedly immediately after (5 minutes after) the administration of ICG-HSA (7) and that the photoacoustic signal intensity immediately after the administration was maintained even 1 day after the administration.

TABLE 4

| | Relative photoacoustic signal intensity |
|---|---|
| Before administration | 1.0 |
| Five minutes after administration | 7.2 |
| One day after administration | 55 |

Evaluation of Amount Transferred into Tumor Mass

To check the tumor accumulation of ICG-HSA, contrast agents were administered to tumor-bearing mice into which the N87 cell line was implanted. ICG-HSA (7) and various contrast agents were administered in blood of the tumor-bearing mice. The tumor accumulation 1 day after the administration was evaluated by fluorescence. The accumulation in ROI of the tumor site was calculated. Table 5 describes the result of the relative tumor accumulation with respect to the ROI value of ICG. As comparative examples, the relative tumor accumulation values of ICG, ICG-HSA (7)-encapsulating liposome particles, and ICG-encapsulating micellar particles are also described. The results demonstrated that ICG-HSA (7) had higher tumor accumulation than other comparative materials.

TABLE 5

| | Material | Relative tumor accumulation |
|---|---|---|
| Comparative Example 1 | ICG | 1.0 |
| Comparative Example 2 | ICG-HSA-encapsulating liposome | 7.2 |
| Comparative Example 3 | ICG-containing nanomicelles | 1.5 |
| Example | ICG-HSA (7) | 55 |

Photoacoustic Imaging of Sentinel Lymph Node

Figure 2:
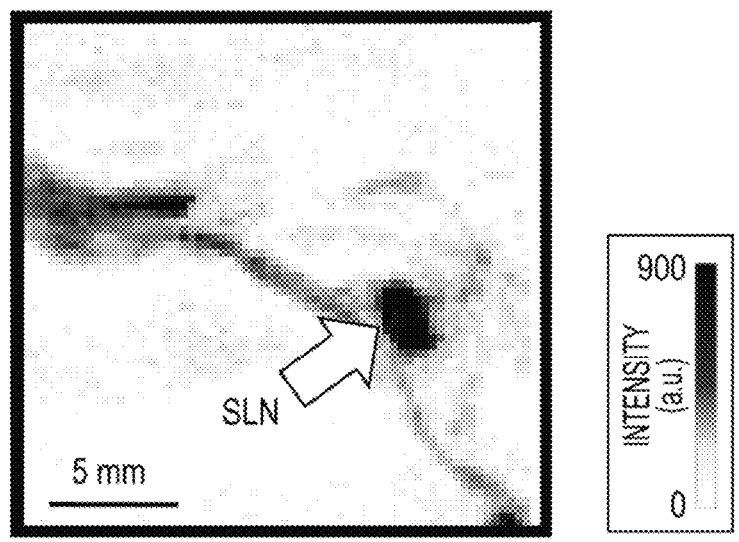
FIG. 2 illustrates the result of measurement of photoacoustic imaging of a nude mouse 1 day after subcutaneous administration of ICG-HSA (7) prepared in an example of the present invention into the plantar surface of the nude mouse.
Figure 3:
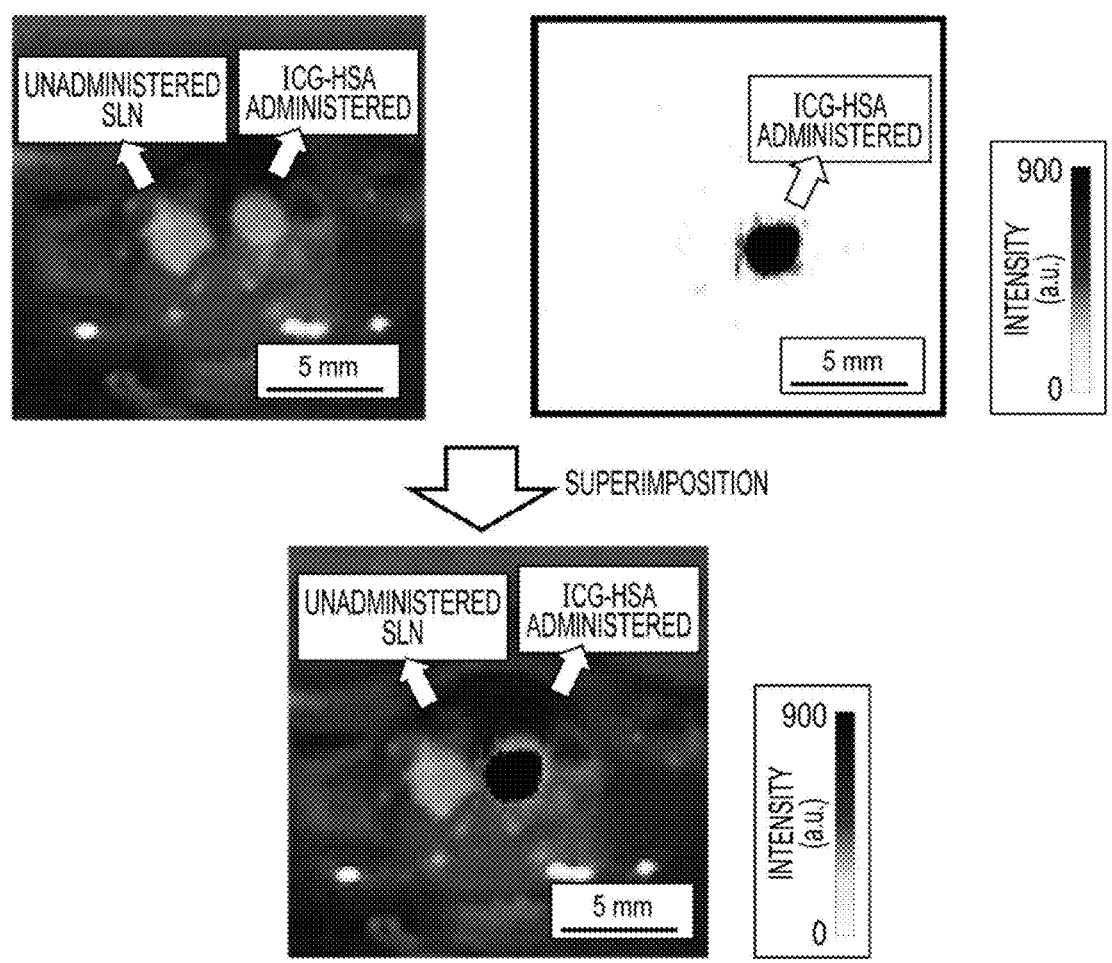
FIG. 3 illustrates the results of measurements of photoacoustic imaging of a sentinel lymph node removed 1 day after subcutaneous administration of ICG-HSA (7) prepared in an example of the present invention into plantar surfaces of nude mice.

The accumulation in a sentinel lymph node (SLN) was evaluated by photoacoustic imaging. First, 130 nmol of ICG-HSA (7) in terms of the amount of the dye was administered subcutaneously into the plantar surface of a nude mouse. Then an evaluation was made as to whether the sentinel lymph node was visualized 1 day after the administration by photoacoustic imaging. Table 6 and FIG. 2 illustrate the results. For ICG and the ICG-containing nanomicelles, substantially no photoacoustic signal was observed from the sentinel lymph nodes 1 day after the administration, so that the sentinel lymph nodes were not visualized. In contrast, for ICG-HSA (7), the SLN was clearly visualized (see FIG. 2), and ICG-HSA (7) had visualization properties substantially the same as ICG-HSA-encapsulating liposome. After the measurement, the SLN was removed. The removed SLN and an SLN into which no contrast agent was administered were juxtaposed to each other and subjected to photoacoustic imaging. FIG. 3 illustrates the results. A significant photoacoustic signal was observed from the SLN 1 day after the administration of ICG-HSA (7), as compared with the unadministered SLN.

TABLE 6

| | Material | Visualization of SLN |
|---|---|---|
| Comparative Example | unadministered | unvisualizable |
| Comparative Example | ICG | unvisualizable |
| Comparative Example | ICG-containing nanomicelles | unvisualizable |
| Comparative Example | ICG-HSA-encapsulating liposome | visualizable |
| Example | ICG-HSA (7) | visualizable |

Evaluation of Accumulation in Sentinel Lymph Node

According to "Evaluation example of accumulation in sentinel lymph node", the accumulation in a sentinel lymph node was evaluated. In this example, 10 nmol of the contrast agent in terms of the amount of the dye was administered to a mouse. Table 7 summarizes the relative accumulation of the contrast agents. As comparative examples, the relative accumulation of ICG, a mixed solution of ICG and HSA, ICG-HSA (7)-encapsulating liposome particles, and ICG-encapsulating micellar particles are also described. The results demonstrated that ICG-HSA (7) exhibited high accumulation in the SLN, compared with the comparative examples.

TABLE 7

| | Material | Relative accumulation |
|---|---|---|
| Comparative Example | ICG | 1.0 |
| Comparative Example | ICG + HSA | 0.6 |
| Comparative Example | ICG-containing nanomicelles | 4.1 |
| Comparative Example | ICG-HSA-encapsulating liposome | 15 |
| Example | ICG-HSA (7) | 22 |

Evaluation of Accumulation of Contrast Agent in Tumor

Aqueous solutions of ICG-HSA (2), ICG-HSA (7), ICG-HSA (21), and ICG-HSA (50) were prepared by the method described in EXAMPLE. Tumor model mice were prepared by subcutaneously implanting Colon 26 cells into BALB/c Slc-nu/nu mice. The aqueous ICG-HSA solutions were intravenously injected in volumes of 100 microliters each (13 nmol in terms of ICG) into the tumor model mice to evaluate the tumor accumulation. Furthermore, in this example, a compound was synthesized by the reaction of ICG-Sulfo-OSu with glycine in a molar ratio of 1:1 (hereinafter, abbreviated as "ICG-Gly") and used as a control sample.

The evaluation of the tumor accumulation was performed as described below. The mice were euthanized with carbon dioxide 24 hours after administration. The tumor tissues were removed and transferred to plastic tubes. An aqueous solution of 1% Triton X-100 was added to each of the tubes in an amount 1.25 times the weight of the tumor tissues. Each of the resulting mixtures was homogenized with a plastic pestle. Then DMSO was added to each mixture in an amount 20.25 times the weight of the tumor tissues to prepare a solution of the dye extracted from the tumor tissues. An aqueous ICG-HSA solution having a known concentration and an aqueous ICG-Gly solution serving as a control were diluted with the solution of the tumor tissues in Triton X-100 to various concentrations. Then DMSO was added to each of the resulting dilute solutions in an amount 20.25 times the amount of each dilute solution to prepare standard solutions for calibration. The fluorescence intensity of the solutions of the dye extracted from the tumor tissues and the standard solutions for calibration was measured with the solutions in the tubes using IVIS (registered trademark) Imaging System 200 Series (XENOGEN Corporation) to quantitatively determine the amount of the dye (% ID/g) in the tumor tissues.

Aqueous solutions of ICG-HSA (2), ICG-HSA (7), ICG-HSA (21), and ICG-HSA (50) were prepared by the method described in EXAMPLE. Tumor model mice were prepared by subcutaneously implanting Colon 26 cells into BALB/c Slc-nu/nu mice. The aqueous ICG-HSA solutions were intravenously injected in volumes of 100 microliters each (13 nmol in terms of ICG) into the tumor model mice to evaluate the tumor accumulation. Furthermore, in this example, an aqueous solution of ICG (available from Pharmaceutical and Medical Device Regulatory Science of Japan) was used as a control sample.

The evaluation of the tumor accumulation was performed as described below. The mice were euthanized with carbon dioxide 24 hours after administration. The tumor tissues were removed and transferred to plastic tubes. An aqueous solution of 1% Triton X-100 was added to each of the tubes in an amount 1.25 times the weight of the tumor tissues. Each of the resulting mixtures was homogenized with a plastic pestle. Then DMSO was added to each mixture in an amount 20.25 times the weight of the tumor tissues to prepare a solution of the dye extracted from the tumor tissues. An aqueous ICG-HSA solution having a known concentration and an aqueous ICG solution were diluted with the solution of the tumor tissues in Triton X-100 to various concentrations. Then DMSO was added to each of the resulting dilute solutions in an amount 20.25 times the amount of each dilute solution to prepare standard solutions for calibration. The fluorescence intensity of the solutions of the dye extracted from the tumor tissues and the standard solutions for calibration was measured with the solutions in the tubes using IVIS (registered trademark) Imaging System 200 Series (XENOGEN Corporation) to quantitatively determine the amount of the dye (% ID/g) in the tumor tissues.

Table 8 describes the accumulation in the Colon 26 cell mass 24 hours after the administration of the aqueous ICG-HSA solutions and the control. The results suggested that the tumor accumulation was improved by covalently binding the dye to HSA, compared with the aqueous ICG solution serving as a control sample. Furthermore, ICG-HSA (7) and ICG-HSA (15) exhibited high values of the ratio of tumor accumulation to blood accumulation 24 hours after the administration. This suggested that they were specifically accumulated in tumor, compared with blood. Moreover, ICG-HSA (7) also exhibited high photoacoustic signal intensity at the tumor site 1 day after the administration. Among these samples, thus, ICG-HSA (7) was most effective in visualizing the tumor.

TABLE 8

| Sample name | Dye labeling index | Tumor accumulation 1 day after administration (% ID/g) | Blood accumulation 1 day after administration (% ID/g) | Ratio of accumulation (tumor/blood) | Relative photoacoustic signal intensity 1 day after administration (signal intensity in administration of ICG = 1.0) |
|---|---|---|---|---|---|
| ICG-HSA (1) | 0.9 | 8.9 | 4.0 | 2.2 | 3.3 |
| ICG-HSA (3) | 1.6 | 8.9 | 2.6 | 3.4 | 2.8 |
| ICG-HSA (7) | 2.3 | 19.7 | 2.3 | 8.6 | 2.3 |
| ICG-HSA (17.5) | 3.0 | 3.0 | 0.2 | 15.0 | 1.8 |
| ICG-HSA (50) | 3.1 | 1.8 | 0.5 | 3.6 | 1.4 |
| ICG | — | 0.1 | 0.2 | 0.5 | 1.0 |

Preparation of Single-Chain Antibody hu4D5-8 scFv

A gene fragment encoding a single-chain antibody (scFv) moiety was prepared on the basis of the gene sequence of the variable region of IgG binding to HER2. A 6×His tag comprising six consecutive histidine residues for protein purification was bound to the C-terminus of the prepared gene. Furthermore, two glycine residues serving as a spacer and a cysteine residue to introduce a signal generating molecule were arranged downstream thereof (SEQ. ID. NO: 1). A plasmid pET-22b (+) (Novagen) in which the foregoing gene fragment was inserted downstream of the T7 promoter was introduced into Escherichia coli BL21 (DE3) to give a strain for expression. After the resulting strain was precultured overnight in 4 mL of an LB-Amp medium, the total volume was added to 250 mL of 2×YT medium and cultured at 28 degrees Celsius with shaking at 120 rpm for 8 hours. Then IPTG was added at a final concentration of 1 mM. The bacteria were cultured overnight at 28 degrees Celsius. The culture of Escherichia coli was centrifuged at 8000×g for 30 minutes at 4 degrees Celsius. The supernatant of the culture was collected Ammonium sulfate of 60% of the weight of the obtained culture was added thereto. Proteins were precipitated by salting out. The solution subjected to salting out was allowed to stand overnight at 4 degrees Celsius and centrifuged at 8000×g for 30 minutes at 4 degrees Celsius to collect precipitates. The resulting precipitates were dissolved in 20 mM Tris HCl/500 mM NaCl buffer. The mixture was dialyzed against 1 L of the buffer. After the dialysis, the protein solution was added to a column filled with His Bind (registered trademark) Resin (Novagen) and purified by metal chelate affinity chromatography using a Ni ion.

(SEQ. ID. NO: 1)
MDIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTFG

QGTKVEIKGGGGSGGGGSGGGGSEVQLVESGGGLVQPGGSLRLSCAASGF

NIKDTYIHWVRQAPGKGLEWVARIYPTNGYTRYADSVKGRFTISADTSKN

TAYLQMNSLRAEDTAVYYCSRWGGDGFYAMDYWGQGTLVTVSSAAALEHH

HHHHGGC

Preparation of Single-Chain Antibody (scFv)-Immobilized ICG-HSA

Human serum albumin (albumin from human serum: HSA, SIGMA) was dissolved in a bicarbonate buffer solution (pH: 8.5) in a concentration of 10 mg/mL to prepare an HSA solution. Then 1 mg of an ICG derivative (ICG-Sulfo-Osu, Dojindo Laboratories) was dissolved in 0.1 mL of DMSO. The resulting DMSO solution was added to the HSA solution in an amount 7 times the molar amount of HSA. The reaction mixture was allowed to stand at 37 degrees Celsius for 2 hours. The reaction mixture was subjected to ultrafiltration (30 kDa) to remove unreacted substances, thereby preparing an aqueous solution of ICG-HSA.

Sulfosuccinimidyl-4-(N-maleimidomethyl)cyclohexane-1-carboxylate (Sulfo-SMCC, PIERCE) was added thereto in an amount 60 times the molar amount of ICG-HSA. The mixture was allowed to stand at 4 degrees Celsius for 1 hour. The resulting reaction mixture was subjected to gel filtration (PD-10), so that the replacement with a phosphate buffer solution (PBS) and the separation of unreacted substances were performed, thereby preparing an aqueous solution of Sulfo-SMCC-modified ICG-HSA.

Tris(2-carboxyethyl)phosphine (TCEP) hydrochloride was added to the single-chain scFv in an amount 14 times the molar amount of the single-chain antibody, scFv. The mixture was reacted at room temperature for 2 hours. Then scFv was mixed with Sulfo-SMCC-modified ICG-HSA prepared as described above in an amount 1 or 2 times the molar amount of Sulfo-SMCC-modified ICG-HSA. The mixture was reacted at room temperature for 5 hours. The reaction mixture was subjected to ultrafiltration (50 kDa) to remove unreacted substances, thereby providing scFv-modified ICG-HSA (scFv-ICG-HSA). A compound prepared by the reaction of scFv in an amount 1 time the molar amount of Sulfo-SMCC-modified ICG-HSA is referred to as "scFv-ICG-HSA-1". A compound prepared by the reaction of scFv in an amount 2 times the molar amount of Sulfo-SMCC-modified ICG-HSA is referred to as "scFv-ICG-HSA-2".

Preparation of scFv-Immobilized HSA (scFv-HSA) and Preparation of ICG-Labeled scFv-HSA (scFv-HSA-ICG)

Sulfosuccinimidyl-4-(N-maleimidomethyl)cyclohexane-1-carboxylate (Sulfo-SMCC, PIERCE) was added to HSA in an amount 60 times the molar amount of HSA. The mixture was allowed to stand at 4 degrees Celsius for 1 hour. The resulting reaction mixture was subjected to gel filtration (PD-10), so that the replacement with a phosphate buffer solution (PBS) and the separation of unreacted substances were performed, thereby preparing an aqueous solution of Sulfo-SMCC-modified HSA.

Tris(2-carboxyethyl)phosphine (TCEP) hydrochloride was added to the single-chain scFv in an amount 14 times the molar amount of the single-chain scFv. The mixture was reacted at room temperature for 2 hours. Then scFv was mixed with Sulfo-SMCC-modified HSA prepared as described above in an amount 3 times the molar amount of Sulfo-SMCC-modified HSA. The mixture was reacted at room temperature for 5 hours. The reaction mixture was subjected to ultrafiltration (50 kDa) to remove unreacted substances, thereby providing scFv-immobilized HSA (scFv-HSA).

ICG was added to scFv-HSA prepared as described above in an amount 7, 21, or 70 times the molar amount of scFv-HSA. The mixture was reacted for 2 hours and subjected to ultrafiltration (30 kDa) to remove unreacted substances, thereby preparing ICG-labeled scFv-HSA (scFv-HSA-ICG). Compounds prepared by the reaction of ICG in amounts 7, 21, and 70 times the molar amount of scFv-HSA are referred to as scFv-HSA-ICG-7, scFv-HSA-ICG-21, and scFv-HSA-ICG-70, respectively.

Calculation of Dye Labeling Index

With respect to ICG-HSA, scFv-ICG-HSA, and scFv-HSA-ICG prepared by the foregoing methods, the dye labeling indices to HSA were calculated. The dye labeling indices were calculated by the quantitative determination of protein using the BCA assay and by the measurement of the concentrations on the basis of the absorbance of ICG. Table 9 describes the results.

Calculation of Number of Single-Chain Antibody (scFv) Immobilized

With respect to scFv-ICG-HSA and scFv-HSA prepared as described above, the number of single-chain antibody molecules (scFv's) immobilized to HSA was calculated. Table 9 describes the results. The number of scFv's immobilized was calculated by performing sodium dodecyl sulfate-polyacrylamide gel electrophoresis (SDS-PAGE) and measuring Coomassie staining intensity of bands.

Evaluation of HER2-Binding Capacity of scFv-ICG-HSA and scFv-HSA-ICG

The interaction between HER2, which is an antigen, and each of the scFv-ICG-HSA and scFv-HSA-ICG complexes prepared as described above was measured with a Biacore X System (GE Healthcare Corp.) to measure HER2-binding capacities. As the antigen, Recombinant Human ErbB2/Fc Chimera (R&D Systems, Inc.) was used. The antigen was immobilized by amine coupling to a carboxymethyldextran chain on a surface of Chip CM5 according to the manufacturer's recommendation. The amount of the antigen immobilized was about 5000 RU. PBS-T (2.68 mM KCl/137 mM NaCl/1.47 mM $KH_2PO_4$/1 mM $Na_2HPO_4$/0.005% Tween 20, pH: 7.4) was used as a running buffer. Concentrations of samples were set to 100 nM to 800 nM. The samples were injected at a flow rate of 20 microliters per minutes to evaluate HER2-binding capacities (dissociation constants $K_D$ [M]). Table 9 describes the results. The results demonstrated that a larger number of scFv's immobilized resulted in a higher HER2-binding capacity. Furthermore, comparison of scFv-HSA-ICG-7, scFv-HSA-ICG-21, and scFv-HSA-ICG-70 revealed that the HER2-binding capacity was markedly reduced at a dye labeling index of 21.

Evaluation of HER2-Specific Tumor Accumulation

To check HER2-specific tumor accumulation of the molecular probes (ICG-HSA, scFv-ICG-HSA, and scFv-HSA-ICG) prepared as described above, an experiment was performed as described below. The molecular probes were administered to tumor-bearing model mice into which the HER2-positive N87 cell line and the HER2-negative SUIT-2 cell line were implanted. The tumors were removed 1 day after the administration. To the tumors, 1% Triton X-100 was added. The mixtures were homogenized. Dimethyl sulfoxide (DMSO) was added to each resulting homogenate in an amount 9 times the amount of the homogenate, thereby preparing a solution. The fluorescence intensity of these solutions was measured to calculate the tumor accumulation [% ID/g] per tumor weight of the molecular probes administered to the mice. Furthermore, a value obtained by dividing the tumor accumulation in N87 by the tumor accumulation in SUIT-2 (N87/SUIT-2) was calculated as a value indicating HER2 specificity. Table 9 describes the results. The results demonstrated that scFv-ICG-HSA-1, scFv-ICG-HSA-2, and scFv-HSA-ICG-7 exhibited HER2-specific accumulation. Comparison of scFv-ICG-HSA-1 and scFv-ICG-HSA-2 revealed that scFv-ICG-HSA-2 having a large number of scFv's immobilized exhibited higher HER2 specificity. This suggested that a larger number of scFv's immobilized resulted in higher HER2 specificity. Comparison of scFv-HSA-ICG-7, scFv-HSA-ICG-21, and scFv-HSA-ICG-70 revealed that when the dye labeling index was 6.6 or more, HER2-specific accumulation was not observed. The reason for this is as follows: scFv-HSA-ICG-7 and scFv-HSA-ICG-21 had the same HER2-binding capacity. Thus, for example, labeling with a large number of ICG molecules possibly promoted hepatic elimination with ICG.

That is, regarding scFv-immobilized ICG-HSA, the results demonstrated that at a dye labeling index of 1.9, when the number of scFv's immobilized was 0.69 or more, HER2-specific accumulation was exhibited, and when the number of scFv's immobilized was 1.7, higher HER2 specificity was exhibited. Regarding ICG-labeled scFv-HSA, the results demonstrated that when the number of scFv's immobilized was 2.9, the dye labeling index was required to be less than at least 6.6. Accordingly, the results suggested that the following conditions were required to achieve HER2-specific tumor accumulation: the number of scFv's immobilized was 0.69 or more and preferably about 1.7 or more, and the dye labeling index was less than 6.6.

TABLE 9

| Sample name | Number of scFv's immobilized | Dye labeling index | $K_D$ to HER2 [M] | Tumor accumulation (after 1 day) [% ID/g] | | HER2 specificity N87/ |
|---|---|---|---|---|---|---|
| | | | | N87 | SUIT-2 | SUIT-2 |
| scFv-ICG-HSA-1 | 0.69 | 1.9 | 5.9E−08 | 1.4 | 0.9 | 1.6 |
| scFv-ICG-HSA-2 | 1.7 | 1.9 | 2.5E−08 | 2.3 | 1.1 | 2.1 |
| scFv-HSA-7 | 2.9 | 2.0 | 1.3E−08 | 1.9 | 0.6 | 3.2 |
| scFv-HSA-21 | 2.9 | 6.6 | 1.4E−08 | 0.6 | 0.5 | 1.2 |
| scFv-HSA-70 | 2.9 | 21 | 8.5E−08 | 0.8 | 0.7 | 1.1 |
| ICG-HSA | — | 2.7 | — | 3.1 | 3.0 | 1.0 |

Comparison of Method for Immobilizing HER2 Capture Molecule on ICG-HSA

Human serum albumin (albumin from human serum: HSA, SIGMA) was dissolved in a bicarbonate buffer solution (pH: 8.5) in a concentration of 10 mg/mL to prepare an HSA solution. Then 1 mg of an ICG derivative (ICG-Sulfo-Osu, Dojindo Laboratories) was dissolved in 0.1 mL of DMSO. The resulting DMSO solution was added to the HSA solution in an amount 7 times the molar amount of HSA. The reaction mixture was allowed to stand at 37 degrees Celsius for 2 hours. The reaction mixture was subjected to ultrafiltration (30 kDa) to remove unreacted substances, thereby preparing an aqueous solution of ICG-HSA.

SM(PEG)2 (succinimidyl[(N-maleimidopropionamido)-diethyleneglycol]ester, PIERCE) or SUNBRIGHT MA-100TS (NOF CORPORATION) was added thereto in an amount 10 or 100 times the molar amount of ICG-HSA. The mixture was allowed to stand at 4 degrees Celsius for 1 hour. The resulting reaction mixture was subjected to gel filtration (PD-10), so that the replacement with a phosphate buffer solution (PBS) and the separation of unreacted substances were performed, thereby preparing aqueous solutions of ICG-HSA modified with two types of linkers in different ratios. The number of molecules of each linker attached to ICG-HSA was calculated from a change in the number of amino acids in ICG-HSA before and after the attachment of the linker. The number of amino acids was quantitatively determined by a color reaction with 2,4,6-trinitrobenzenesulfonic acid.

Affibody (registered trademark, Affibody) is a polypeptide serving as a HER2 capture molecule. Dithiothreitol (NACALAI TESQUE, INC.) was added at a final concentration of 20 mM to a phosphate buffer solution containing Affibody (registered trademark) dissolved therein. The mixture was stirred at 25 degrees Celsius for 2 hours. The reaction mixture was subjected to gel filtration (PD-10) to remove dithiothreitol, thereby preparing an aqueous solution of Affibody (registered trademark) subjected to reduction treatment. This aqueous solution was mixed with each of the aqueous solutions of ICG-HSA modified with two types of linkers in different ratios. The mixtures were stirred at 25 degrees Celsius for 2 hours or more. Then the mixtures were subjected to ultrafiltration (30 kDa) to remove unreacted Affibody (registered trademark), thereby preparing Affibody (registered trademark)-immobilized ICG-HSA. The number of Affibody (registered trademark) molecules immobilized was calculated by quantitatively determining unfixed molecules eluted in the filtrate by the ultrafiltration. Here, Affibody (registered trademark)-immobilized ICG-HSA prepared by the use of SM(PEG)2 as the linker in an amount 10 times the molar amount of ICG-HSA is referred to as L1-ICG-HSA. Affibody (registered trademark)-immobilized ICG-HSA prepared by the use of SM(PEG)2 as the linker in an amount 100 times the molar amount of ICG-HSA is referred to as L2-ICG-HSA. Similarly, Affibody (registered trademark)-immobilized ICG-HSA prepared by the use of SUNBRIGHT MA-100TS as the linker in an amount 10 times the molar amount of ICG-HSA is referred to as L3-ICG-HSA. Affibody (registered trademark)-immobilized ICG-HSA prepared by the use of SUNBRIGHT MA-100TS as the linker in an amount 100 times the molar amount of ICG-HSA is referred to as L4-ICG-HSA. The binding affinity of Affibody (registered trademark)-immobilized ICG-HSA for HER2, which was a target molecule, was evaluated by a surface plasmon resonance (SPR) method. SPR was measured with ProteOn (registered trademark) XPR36 (Bio-Rad Laboratories, Inc). Recombinant Human ErbB2/Fc Chimera (R&D Systems, Inc.) was dissolved in an acetic acid buffer (pH: 5.0) and immobilized by amine coupling to carboxy groups on a surface of a GLM sensor chip. The amount immobilized was about 3000 RU (resonance unit). Each sample of Affibody (registered trademark)-immobilized ICG-HSA was diluted with a phosphate buffer containing 0.005% Tween 20 (pH: 7.4) to various concentrations and injected into a flow cell at a flow rate of 50 microliters per minute. With respect to the measurement time, the injection time (binding) was 120 seconds, and the elapsed time after termination of the injection (dissociation) was 120 seconds. In experiments for the analysis of binding kinetics, sensorgrams were analyzed by a 1:1 Langmuir fitting model. Table 10 summarizes calculated binding dissociation constants ($K_D$). Each of the samples had a binding affinity to HER2. It was suggested that in particular, the sample in which a large number of HER2 capture molecules were immobilized by the use of SM(PEG)2 in an amount 100 times had a higher binding affinity to HER2.

TABLE 10

| Sample name | Type of linker | Ratio of linker fed for reaction (linker/ICG-HSA) | Number of linkers attached (linker/ICG-HSA) | Ratio of HER2-binding molecules fed for reaction (HER2-binding molecules/ICG-HSA) | Number of HER2-binding molecules attached (HER2-binding molecules/ICG-HSA) | Binding affinity to HER2 ($K_D$) [nM] |
|---|---|---|---|---|---|---|
| L1-ICG-HSA | SM(PEG)2 | 10 | 5.0 | 10 | 3.0 | 2.3 |
| L2-ICG-HSA | SM(PEG)2 | 100 | 8.6 | 10 | 5.0 | 0.24 |
| L3-ICG-HSA | SUNBRIGHT MA-100TS | 10 | 0.7 | 10 | 0.5 | 4.1 |
| L4-ICG-HSA | SUNBRIGHT MA-100TS | 100 | 2.2 | 10 | 1.9 | 11 |

Comparison of Types of Combinations of HER2-Binding Molecules and Linkers

Human serum albumin (albumin from human serum: HSA, SIGMA) was dissolved in a bicarbonate buffer solution (pH: 8.5) in a concentration of 10 mg/mL to prepare an HSA solution. Then 1 mg of an ICG derivative (ICG-Sulfo-Osu, Dojindo Laboratories) was dissolved in 0.1 mL of DMSO. The resulting DMSO solution was added to the HSA solution in an amount 7 times the molar amount of HSA. The reaction mixture was allowed to stand at 37 degrees Celsius for 2 hours. The reaction mixture was subjected to ultrafiltration (30 kDa) to remove unreacted substances, thereby preparing an aqueous solution of ICG-HSA.

SM(PEG)2, SMCC (succinimidyl 4-[N-maleimidomethyl]cyclohexane-1-carboxylate, PIERCE), or BS(PEG)5 (bis-N-succinimidyl-(pentaethylene glycol) ester, PIERCE) was added thereto in an amount 100 times the molar amount of ICG-HSA. The mixture was allowed to stand at 4 degrees Celsius for 1 hour. The resulting reaction mixture was subjected to gel filtration (PD-10), so that the replacement with a phosphate buffer solution (PBS) and the separation of unreacted substances were performed, thereby preparing aqueous solutions of ICG-HSA modified with three types of linkers. The number of molecules of each linker attached to ICG-HSA was calculated from a change in the number of amino acids in ICG-HSA before and after the attachment of the linker. The number of amino acids was quantitatively determined by a color reaction with 2,4,6-trinitrobenzenesulfonic acid. The number of linker molecules in ICG-HSA modified with SM(PEG)2 (hereinafter, abbreviated as "SM-ICG-HSA") was 13. The number of linker molecules in ICG-HSA modified with SMCC (hereinafter, abbreviated as "CC-ICG-HSA") was 9. The number of linker molecules in ICG-HSA modified with BS(PEG)5 (hereinafter, abbreviated as "BS-ICG-HSA") was 15.

Next, scFv, Affibody (registered trademark), or HER2-binding peptides were immobilized to ICG-HSA modified with the three types of linkers described above. The sequences of the HER2-binding peptide were described below.

```
                                        (SEQ. ID. NO: 2)
YCDGFYACYMDVGGKGSK (SEQ. ID. NO: 3)
MARSGLGGKGSC
```

In the case of the immobilization to ICG-HSA modified with the linkers, scFv was subjected to reduction treatment with TCEP, and Affibody (registered trademark) was subjected to reduction treatment with dithiothreitol, in the same ways as described above in advance. One of the linker-modified ICG-HSA samples was mixed with the HER2-binding peptide, Affibody (registered trademark) subjected to reduction treatment, or scFv subjected to reduction treatment. The mixture was stirred at 25 degrees Celsius for 2 hours or more. Then the mixture was subjected to ultrafiltration (30 kDa) to remove unreacted HER2-binding molecules, thereby preparing HER2-binding-molecule-immobilized ICG-HSA. The number of the HER2-binding molecules immobilized was calculated by quantitatively determining unfixed molecules eluted in the filtrate by the ultrafiltration. Here, BS-ICG-HSA to which the peptide of SEQ. ID. NO: 2 was immobilized is referred to as L5-ICG-HSA. SM-ICG-HSA to which the peptide of SEQ. ID. NO: 3 was immobilized is referred to as L6-ICG-HSA. CC-ICG-HSA to which the peptide of SEQ. ID. NO: 3 was immobilized is referred to as L7-ICG-HSA. BS-ICG-HSA to which the peptide of SEQ. ID. NO: 3 was immobilized is referred to as L8-ICG-HSA. SM-ICG-HSA to which Affibody (registered trademark) was immobilized is referred to as L9-ICG-HSA. CC-ICG-HSA to which Affibody (registered trademark) was immobilized is referred to as L10-ICG-HSA. BS-ICG-HSA to which Affibody (registered trademark) was immobilized is referred to as L11-ICG-HSA. scFv-immobilized SM-ICG-HSA is referred to as L12-ICG-HSA. scFv-immobilized CC-ICG-HSA is referred to as L13-ICG-HSA. scFv-immobilized BS-ICG-HSA is referred to as L14-ICG-HSA. The binding affinities of these HER2-binding-molecule-immobilized ICG-HSA samples for HER2, which was a target molecule, were evaluated by the surface plasmon resonance (SPR) method. SPR was measured with ProteOn (registered trademark) XPR36 (Bio-Rad Laboratories, Inc.) as described above.

In the evaluation of tumor accumulation, female outbred BALB/c Slc-nu/nu mice (6 weeks old on purchase) (Japan SLC Inc.) were used. The mice were acclimated using standard feeds and beddings and given food and drinking water ad libitum for 1 week before cancer cells were transplanted. At approximately 1 week before an imaging experiment, $1 \times 10^6$ Colon 26 mouse colon cancer cells (Riken, Japan) were subcutaneously injected into the right shoulder and the right thigh of each mouse, and $1 \times 10^6$ Colon 26 mouse colon cancer cells into which the HER2 gene was artificially transferred were subcutaneously injected into the left shoulder and the left thigh of each mouse. Tumor cells had been all established by the time of the experiment. The body weights of the mice were between 17 and 22 g. Then 200 microliters (13 nmol in terms of ICG) of HER2-binding-molecule-immobilized ICG-HSA or ICG-HSA to which nothing was immobilized was intravenously injected into the tumor-bearing mice. The mice were euthanized with carbon dioxide 24 hours after administration. The tumor tissues were removed and transferred to plastic tubes. An aqueous solution of 1% Triton X-100 was added to each of the tubes in an amount 1.25 times the weight of the tumor tissues. Each of the resulting mixtures was homogenized with a plastic pestle. Then DMSO was added to each mixture in an amount 20.25 times the weight of the tumor tissues to prepare a solution of the dye extracted from the tumor tissues. Meanwhile, the tumor tissues were removed from tumor-bearing mice into which HER2-binding-molecule-immobilized ICG-HSA was not administered. The tumor tissues were transferred to plastic tubes. An aqueous solution of 1% Triton X-100 was added to each of the tubes in an amount 1.25 times the weight of the tumor tissues. Each of the resulting mixtures was homogenized with a plastic pestle to prepare a solution of the tumor tissues in Triton-X100. A HER2-binding-molecule-immobilized ICG-HSA solution having a known concentration was diluted with the solution of the tumor tissues in Triton X-100 to various concentrations. Then DMSO was added to each of the resulting dilute solutions in an amount 20.25 times the amount of each dilute solution to prepare standard solutions for calibration. The fluorescence intensity of the solutions of the dye extracted from the tumor tissues and the standard solutions for calibration was measured with the solutions in the tubes using IVIS (registered trademark) Imaging System 200 Series (XENOGEN Corporation) to quantitatively determine the amount of the dye in the tumor tissues. Table 11 summarizes the number of linkers immobilized to HER2-binding-molecule-immobilized ICG-HSA, the number of HER2-binding molecules, the binding affinity to HER2 in vitro, the accumulation in the Colon 26 tumor into which the HER2 gene was transferred, and the ratio of the accumulation in the Colon 26 tumor into which the HER2 gene was transferred to the accumulation in the wild-type Colon 26 tumor. In all HER2-binding-molecule-immobilized ICG-HSA samples except L11-ICG-HSA, although the accumulation was reduced, selective accumulation in the Colon 26 tumor into which the HER2 gene was transferred was observed with respect to the wild-type Colon 26 tumor, compared with ICG-HSA into which nothing was immobilized. In the case of L11-ICG-HSA, it is thought that HER2 selectivity was not provided because of the effects of an increase in molecular weight and a reduction in binding affinity to HER2. Comparison of the HER2-binding molecules revealed that scFv had the highest HER2 selectivity. Comparison of the linkers attached to ICG-HSA revealed that SM(PEG)2 or SMCC tended to provide high HER2 selectivity.

TABLE 11

| Sample name | Type of HER2-binding molecules | Type of linker | Number of linker | Number of HER2-binding molecules | Binding affinity to HER2 (KD) [nM] | HER2-positive tumor accumulation [% ID/g] | HER2 selectivity |
|---|---|---|---|---|---|---|---|
| L5-ICG-HSA | peptide (SEQ. ID. No. 2) | BS(PEG)5 | 15 | 2.7 | 3940 | 2.0 | 1.4 |
| L6-ICG-HSA | peptide (SEQ. ID. No. 3) | SMCC | 9 | 8.7 | 380 | 4.2 | 1.4 |
| L7-ICG-HSA | peptide (SEQ. ID. No. 3) | SM(PEG)2 | 13 | 10.3 | 94.5 | 8.4 | 0.8 |
| L8-ICG-HSA | peptide (SEQ. ID. No. 3) | BS(PEG)5 | 15 | 2.4 | 1160 | 0.7 | 1.0 |
| L9-ICG-HSA | Affibody (registered trademark) | SMCC | 9 | 4.1 | 10.0 | 3.5 | 1.7 |
| L10-ICG-HSA | Affibody (registered trademark) | SM(PEG)2 | 13 | 3.9 | 16.9 | 1.6 | 0.9 |
| L11-ICG-HSA | Affibody (registered trademark) | BS(PEG)5 | 15 | 2.8 | 290 | 1.2 | 0.7 |
| L12-ICG-HSA | scFv | SMCC | 9 | 0.5 | 1.93 | 2.2 | 1.4 |
| L13-ICG-HSA | scFv | SM(PEG)2 | 13 | 0.5 | 3.65 | 1.6 | 1.4 |
| L14-ICG-HSA | scFv | BS(PEG)5 | 15 | 0.5 | 20.2 | 2.4 | 2.0 |
| ICG-HSA | — | — | — | — | unmeasurable | 9.6 | 0.7 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-161643, filed Jul. 20, 2012, which is hereby incorporated by reference herein in its entirety.

The invention claimed is:

1. A contrast agent for photoacoustic imaging, comprising:
a complex including albumin covalently bound to at least one organic dye that absorbs light in a near-infrared wavelength region, wherein the complex has a structure represented by formula (I):

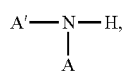

wherein, in the formula (I), A represents a site of the albumin with one amino group removed, A' is an organic dye represented by formula (i) or formula (ii), and * in each of the formulae (i) and (ii) represents a bond with a nitrogen atom (N) in the formula (I), and wherein on average in the contrast agent, a number of molecules of the at least one organic dye covalently bound to the albumin of the complex is 1.6 or more:

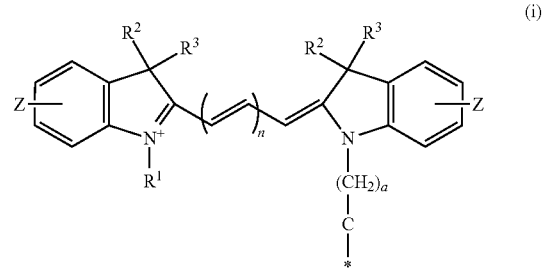

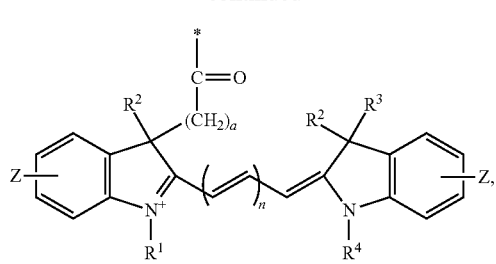

wherein, in the formulae (i) and (ii), Z's each represent a hydrogen atom, a sulfonic group, or a cyclic aromatic ring selected from the group consisting of a benz[e]indole ring, a benz[f]indole ring, and a benz[g]indole ring formed together with an indole ring bound to a corresponding one of Z's; and hydrogen atoms of the cyclic aromatic ring each may be replaced with an alkyl group having 1 to 10 carbon atoms, an alkoxy group having 1 to 10 carbon atoms, or a sulfonic group, wherein, in the formulae (i) and (ii), $R^1$'s each represent an alkyl group having 1 to 10 carbon atoms or —$(CH_2)_b$—$SO_3^-$, wherein b represents an integer of 1 to 10; when $R^1$'s each represent an alkyl group, a halide ion or an organic acid ion may be contained as a counter ion; and $R^2$'s and $R^3$'s each independently represent a hydrogen atom, an alkyl group having 1 to 10 carbon atoms, an alkoxy group having 1 to 10 carbon atoms, —$(CH_2)_b$—$SO_3^-$, wherein b represents an integer of 1 to 10, or —$(CH_2)_b$—$SO_3X$, wherein b represents an integer of 1 to 10, and X represents sodium, potassium, ammonium, triethylammonium, lysine, or arginine, wherein, in the formulae (i) and (ii), a's each represent an integer of 1 to 10; and n's each represent 2 or 3, and wherein, in the formula (ii), $R^4$ represents an alkyl group having 1 to 10 carbon atoms or —$(CH_2)_b$—$SO_3X$, wherein b represents an integer of 1 to 10, and X represents sodium, potassium, ammonium, triethylammonium, lysine, or arginine.

2. The contrast agent for photoacoustic imaging according to claim 1, wherein the formula (i) is represented by any one of formulae (i-1) to (i-6):

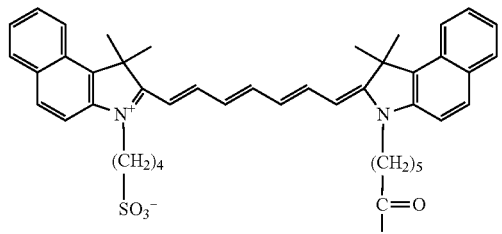

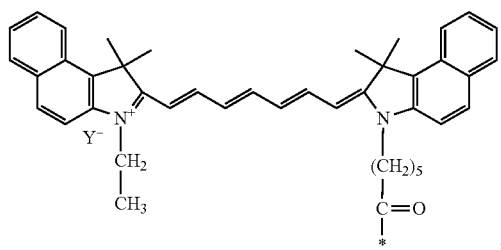

wherein, in the formula (i-2), $Y^-$ represents a halide ion or an organic acid ion,

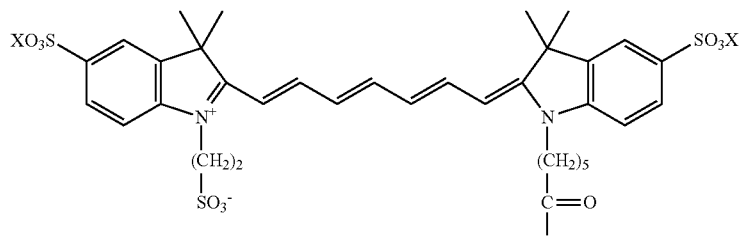

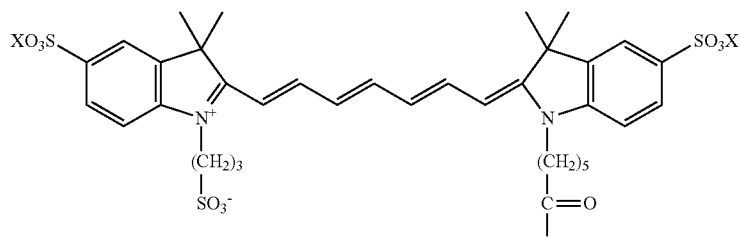

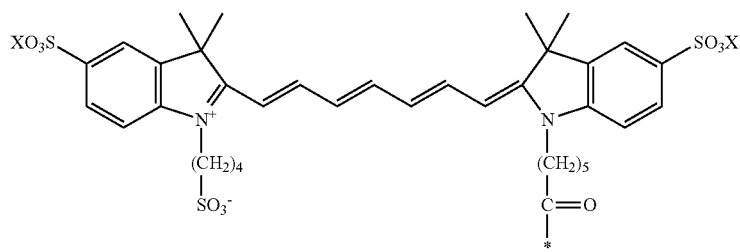

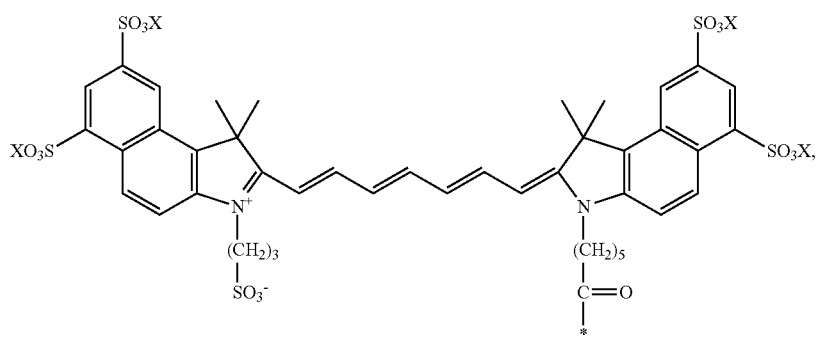

wherein, in the formulae (i-3) to (i-6), X's each represent sodium, potassium, ammonium, triethylammonium, lysine, or arginine.

3. The contrast agent for photoacoustic imaging according to claim 1, wherein the formula (ii) is represented by formula (ii-1) or (ii-2):

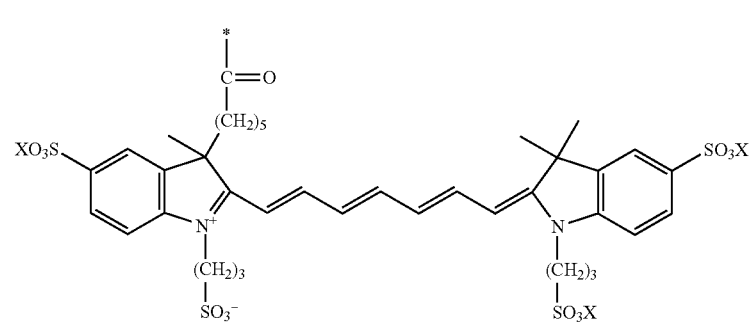

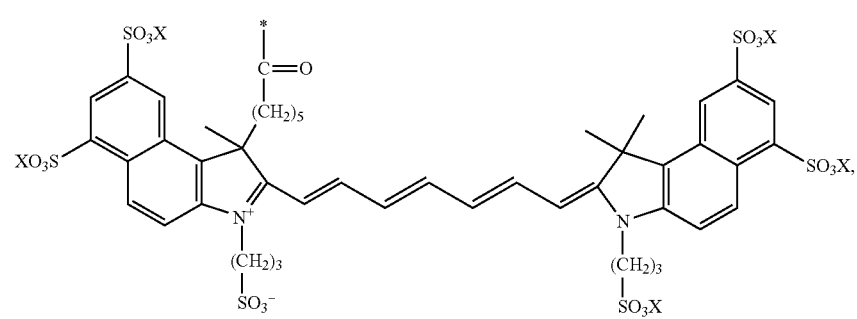

wherein, in the formulae (ii-1) and (ii-2), X's each represent sodium, potassium, ammonium, triethylammonium, lysine, or arginine.

4. The contrast agent for photoacoustic imaging according to claim 1, wherein the complex is represented by formula (I-1):

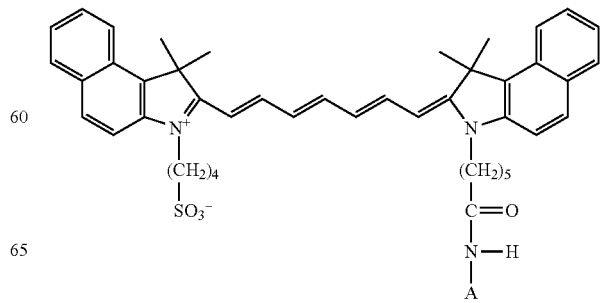

5. The contrast agent for photoacoustic imaging according to claim 1, wherein the complex is in a form of particles, and a hydrodynamic average particle size of the particles is 200 nm or less when measured by a dynamic light scattering method.

6. The contrast agent for photoacoustic imaging according to claim 1, further comprising a capture molecule and/or an addition agent.

7. The contrast agent for photoacoustic imaging according to claim 1, wherein on average in the contrast agent, the number of molecules of the at least one organic dye covalently bound to the albumin of the complex is 2.3 or more.

8. The contrast agent for photoacoustic imaging according to claim 1, wherein on average in the contrast agent, the number of molecules of the at least one organic dye covalently bound to the albumin of the complex is from 1.6 to less than 6.6.

9. The contrast agent for photoacoustic imaging according to claim 1, wherein on average in the contrast agent, the number of molecules of the at least one organic dye covalently bound to the albumin of the complex is from 1.6 to 3.1.

10. The contrast agent for photoacoustic imaging according to claim 1, wherein on average in the contrast agent, the number of molecules of the at least one organic dye covalently bound to the albumin of the complex is from 1.6 to 3.0.

* * * * *

```
                      SEQUENCE LISTING

<160> NUMBER OF SEQ ID NOS: 3

<210> SEQ ID NO 1
<211> LENGTH: 257
<212> TYPE: PRT
<213> ORGANISM: Artificial Sequence
<220> FEATURE:
<223> OTHER INFORMATION: Synthesized

<400> SEQUENCE: 1

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
            115                 120                 125
```

```
Glu Ser Gly Gly Gly Leu Val Gln Pro Gly Gly Ser Leu Arg Leu Ser
    130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240

Val Ser Ser Ala Ala Ala Leu Glu His His His His His His Gly Gly
                245                 250                 255

Cys

<210> SEQ ID NO 2
<211> LENGTH: 18
<212> TYPE: PRT
<213> ORGANISM: Artificial Sequence
<220> FEATURE:
<223> OTHER INFORMATION: HER2 binding peptide

<400> SEQUENCE: 2

Tyr Cys Asp Gly Phe Tyr Ala Cys Tyr Met Asp Val Gly Gly Lys Gly
1               5                   10                  15

Ser Lys

<210> SEQ ID NO 3
<211> LENGTH: 12
<212> TYPE: PRT
<213> ORGANISM: Artificial Sequence
<220> FEATURE:
<223> OTHER INFORMATION: HER2 binding peptide

<400> SEQUENCE: 3

Met Ala Arg Ser Gly Leu Gly Gly Lys Gly Ser Cys
1               5                   10
```